US011771803B2

(12) United States Patent
Helms et al.

(10) Patent No.: US 11,771,803 B2
(45) Date of Patent: *Oct. 3, 2023

(54) ENHANCEMENT OF OSTEOGENIC POTENTIAL OF BONE GRAFTS

(71) Applicant: The Board of Trustees of the Leland Stanford Junior University, Stanford, CA (US)

(72) Inventors: Jill Helms, Stanford, CA (US); Girija Dhamdhere, San Jose, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 898 days.

This patent is subject to a terminal disclaimer.

(21) Appl. No.: 16/743,837

(22) Filed: Jan. 15, 2020

(65) Prior Publication Data
US 2020/0147267 A1 May 14, 2020

Related U.S. Application Data

(63) Continuation of application No. 15/868,395, filed on Jan. 11, 2018, now Pat. No. 10,568,989, which is a continuation of application No. 15/063,317, filed on Mar. 7, 2016, now Pat. No. 9,925,304, which is a continuation of application No. 14/333,220, filed on Jul. 16, 2014, now Pat. No. 9,301,980.

(60) Provisional application No. 61/957,946, filed on Jul. 16, 2013.

(51) Int. Cl.
*A61K 9/127* (2006.01)
*A61K 35/28* (2015.01)
*C12N 5/0775* (2010.01)
*A61L 27/36* (2006.01)
*A61K 38/17* (2006.01)
*A61K 35/12* (2015.01)

(52) U.S. Cl.
CPC .......... *A61L 27/3687* (2013.01); *A61K 9/127* (2013.01); *A61K 35/28* (2013.01); *A61K 38/1709* (2013.01); *A61L 27/365* (2013.01); *C12N 5/0663* (2013.01); *A61K 2035/124* (2013.01); *A61L 2430/02* (2013.01); *C12N 2501/415* (2013.01)

(58) Field of Classification Search
None
See application file for complete search history.

(56) References Cited

U.S. PATENT DOCUMENTS

| 2003/0027151 A1 | 2/2003 | Warman et al. |
| 2005/0136042 A1 | 6/2005 | Betz et al. |
| 2005/0261181 A1 | 11/2005 | Wu et al. |
| 2008/0226707 A1 | 9/2008 | Helms et al. |
| 2010/0247494 A1 | 9/2010 | Gregory et al. |
| 2012/0115788 A1 | 5/2012 | Helms |

FOREIGN PATENT DOCUMENTS

| CN | 1846793 | 10/2016 |
| WO | 2008/109119 A2 | 9/2008 |
| WO | WO2009073186 | 11/2009 |
| WO | 2012/034070 A1 | 3/2012 |
| WO | 2012/135176 A2 | 10/2012 |

OTHER PUBLICATIONS

Pilitsis et al., Neurosurg Focus. Dec. 15, 2002;13(6):e1. (Year: 2002).*
Bodine, "Wnt signaling control of bone cell apoptosis", Cell Res., Jan. 22, 2008, pp. 248-253, 18(2), Macmillan Publishers Limited, Basingstoke, United Kingdom.
Bradley et al., "A soluble form of Wnt-1 protein with mitogenic activity on mammary epithelial cells", Mol. Cell Biol., Aug. 1995, pp. 4616-4622, vol. 15 No. 8, American Society for Microbiology, Washington DC.
Clevers, "Wnt signaling: Ig-norrin the dogma.", Curr. Biol., Jun. 8, 2004, pp. R436-R437, 14(11), Elsevier, Amsterdam, Netherlands.
Dimitriou et al., "Bone regeneration: current concepts and future directions", BMC Med., May 31, 2011, pp. 1-10, 9:66, BioMed Central Ltd., London, United Kingdom.
Gaston et al., "Inhibition of fracture healing ", J Bone Joint Surg Br., Dec. 5, 2007, pp. 1553-1560, 89(12), British Editorial Society of Bone and Joint Surgery, London, United Kingdom.
Gaur et al., "Canonical WNT Signaling Promotes Osteogenesis by Directly Stimulating Runx2 Gene Expression", J Biol Chem, Sep. 30, 2005, pp. 33132-33140, 280(39), American Society for Biochemistry and Molecular Biology, Rockville, MD.
Gordon et al., "Wnt signaling: multiple pathways, multiple receptors, and multiple transcription factors", J. Biol. Chem., Aug. 11, 2006, pp. 22429-22433, 281(32), American Society for Biochemistry and Molecular Biology, Rockville, MD.
Hsieh et al., "Biochemical characterization of Wnt-frizzled interactions using a soluble, biologically active vertebrate Wnt protein", Proc. Natl. Acad. Sci. USA, Mar. 30, 1999, pp. 3546-3551, vol. 96 No. 7, PNAS, Washington, DC.
Leucht et al., "Wnt3a Reestablishes Osteogenic Capacity to Bone Grafts from Aged Animals", J. Bone Joint Surg. Am., Jul. 17, 2013, pp. 1278-1288, 95(14), The Journal of Bone and Joint Surgery, Inc., Needham, MA.
Minear et al., "rBMP represses Wnt signal.ing and influences skeletal, progenitor cell fate specification during bone repair", J Bone Miner Res., Jun. 2010, pp. 1196-1207, vol. 25, Issue 6, The Journal. of Bone and Joint Surgery, Inc., Needham, MA.
Minear et al., "Wnt proteins promote bone regeneration", Sci. Transl. Med., Apr. 28, 2010, pp. 1-9, vol. 2, Issue 29, 29ra30, American Association for the Advancement of Science, Washington, D.C.

(Continued)

Primary Examiner — Daniel C Gamett
(74) Attorney, Agent, or Firm — Pamela J. Sherwood; Bozicevic, Field & Francis LLP

(57) ABSTRACT

The present invention concerns the enhancement of the osteogenic potential of bone graft by ex vivo treatment with a Wnt polypeptide, such as a liposomal Wnt polypeptide.

18 Claims, 26 Drawing Sheets
(26 of 26 Drawing Sheet(s) Filed in Color)
Specification includes a Sequence Listing.

(56) References Cited

OTHER PUBLICATIONS

Morrell et al., "Liposomal, packaging generates Wnt protein with in vivo biological. activity", PLoS One, Aug. 13, 2008, pp. 1-9, 3(8), e92930, PLoS One, San Francisco, CA.

Nelson et al., "Convergence of Wnt, beta-catenin, and cadherin pathways", Science, Mar. 5, 2004, pp. 1483-1487, vol. 303, Issue 5663, American Association for the Advancement of Science, Washington, D.C.

Popelut et al., "The acceleration of implant osseointegration by liposomal. Wnt3a", Biomaterial.s, Dec. 2010, pp. 9173-9918, vol. 31, Issue 35, Elsevier, Amsterdam, Netherlands.

Sykaras et al., "Effect of recombinant human bone morphogenetic protein-2 on the osseointegration of dental Implants: a biomechanics study", Clinical Oral Investigations, Dec. 2004, pp. 196-205, vol. 8, Issue 4, Springer, Berlin, Germany.

Tabata et al., "Role of Leukotriene B4 in Monocrotaline-induced Pulmonary Hypertension", The Japanese journal of horacic diseases, 1997, pp. 160-166, vol. 35, No. 2, The Japanese Respiratory Society, Tokyo, Japan.

Van Leeuwen et al., "Biological activity of soluble wingless protein in cultured *Drosophila imaginal* disc cells",Nature, Mar. 24, 1994, pp. 342-344, 368 (6369), Springer, Berlin, Germany.

Zhao et al., "Controlling the in vivo activity of Wnt liposomes", Methods Enzymol, 2009, pp. 331-347, vol. 465, Elsevier, Amsterdam, Netherlands.

Zhang et al., "Wnt/&bgr;—Catenin Signaling Induces the Aging of Mesenchymal Stem Cells through the DNA Damage Response and the p53/p21 Pathway", PLoS One, Jun. 21, 2011, p. 1-12, e21397, vol. 6, Issue 6, PLoS, Francisco, CA.

\* cited by examiner

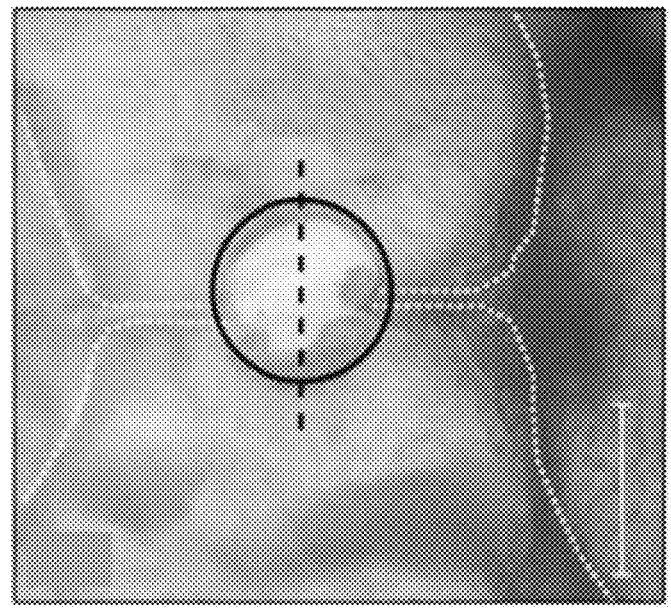
FIG. 1A
FIG. 1B
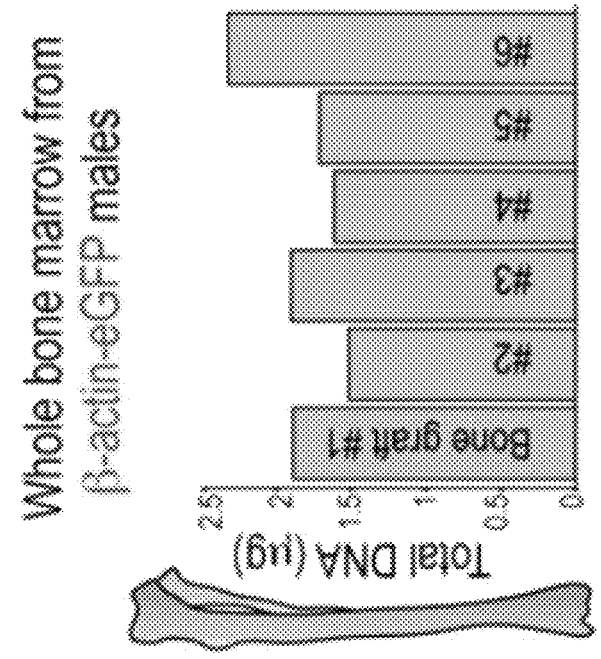
FIG. 1C
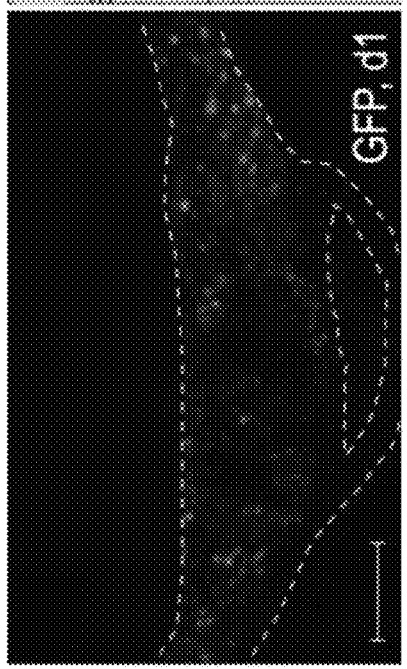
FIG. 1D

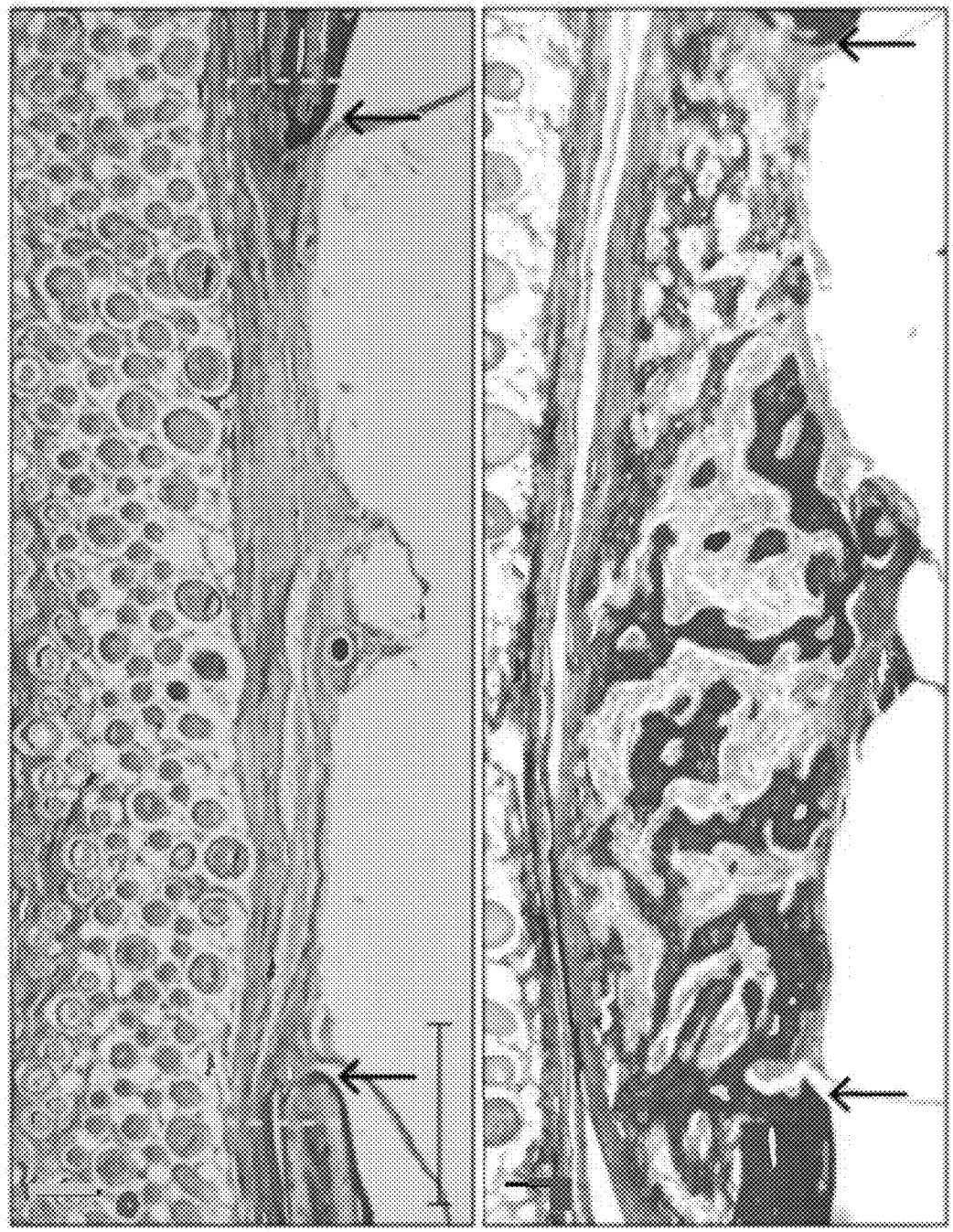

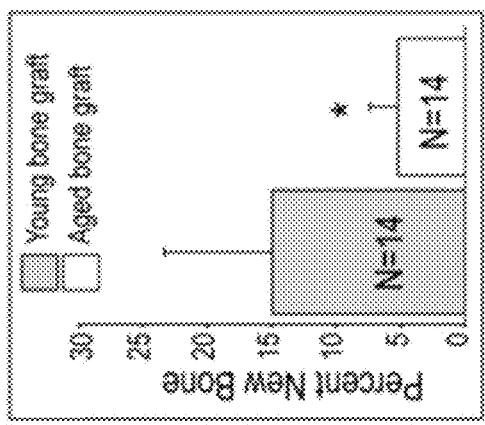
FIG. 2A
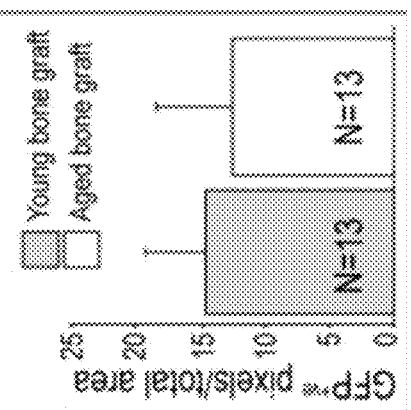
FIG. 2B FIG. 2C
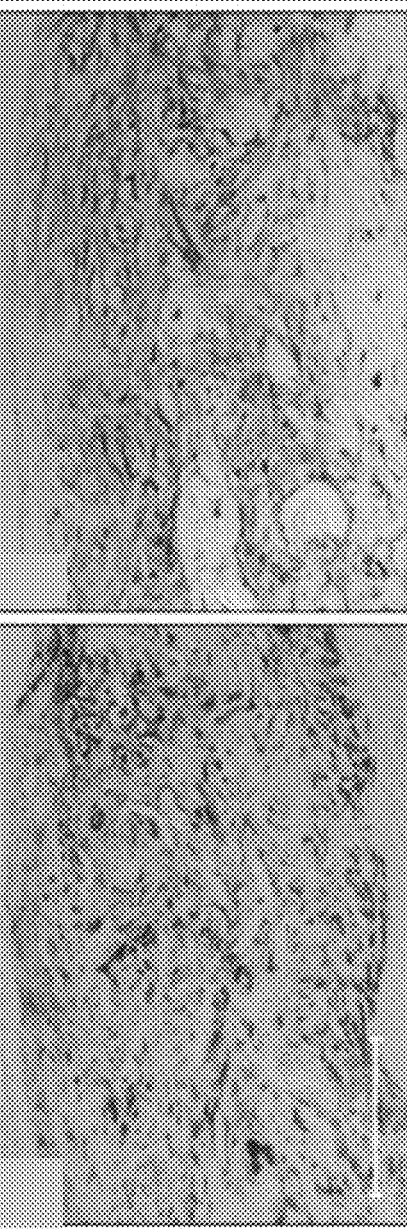
FIG. 2D FIG. 2E FIG. 2F

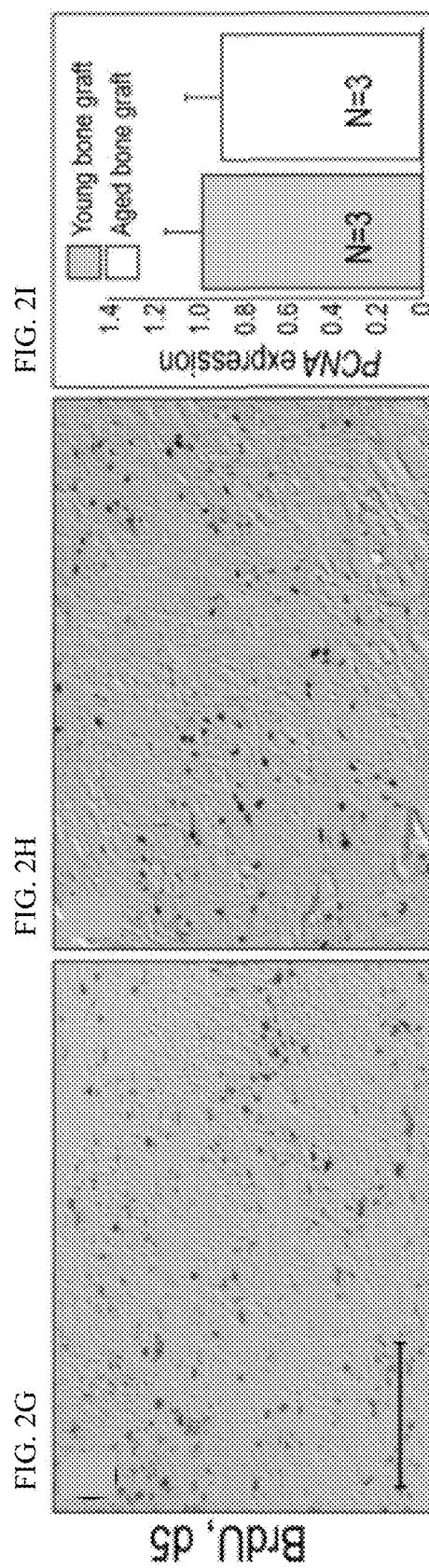

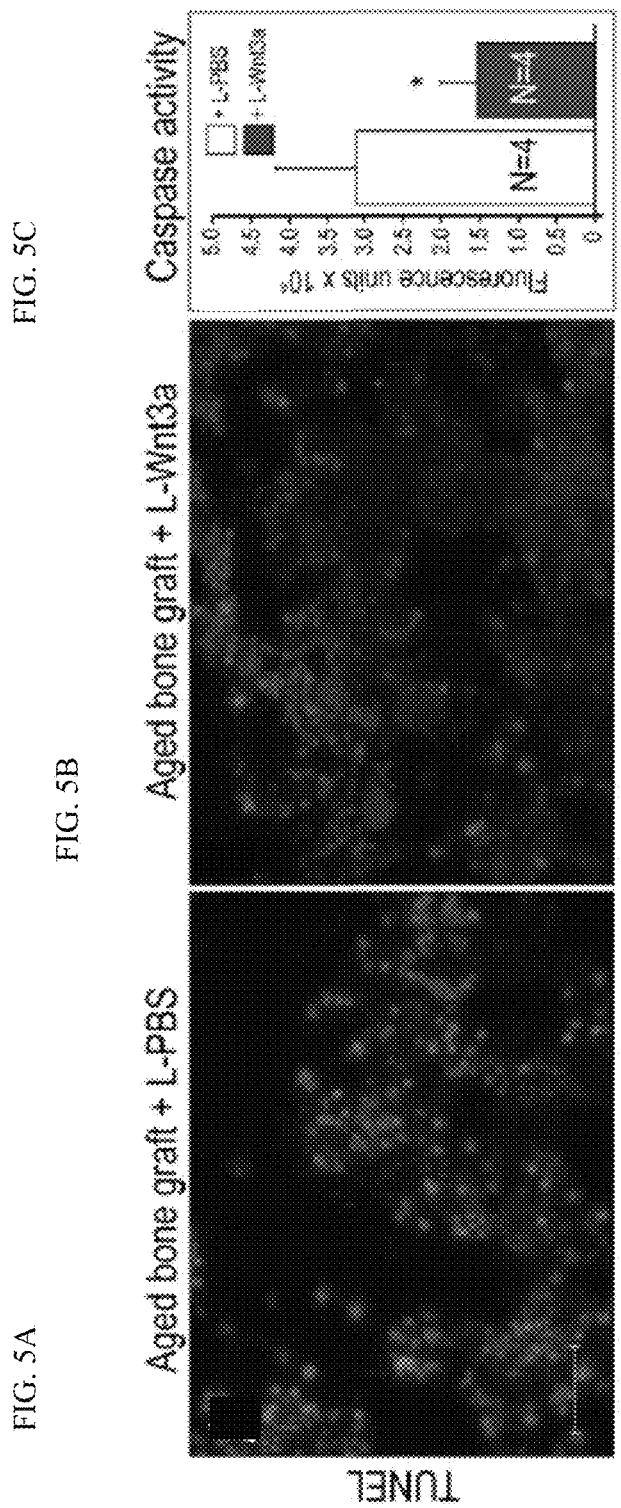

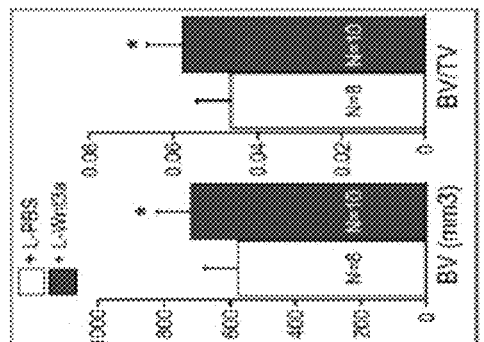
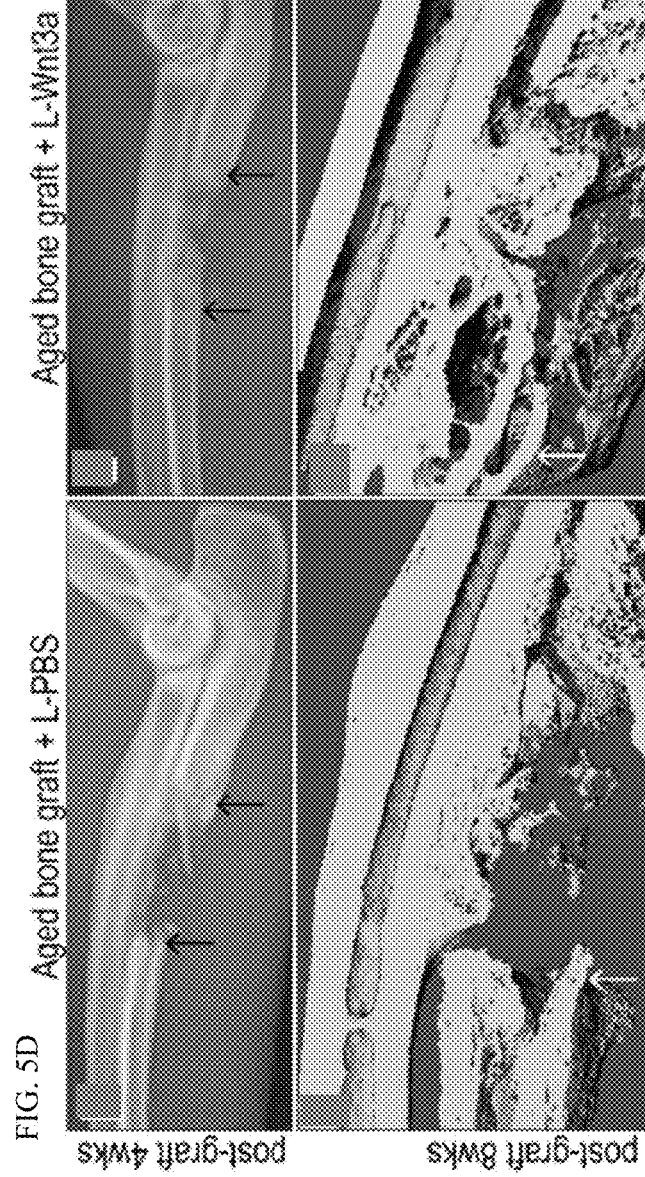
FIG. 5D  FIG. 5E
FIG. 5F  FIG. 5G  FIG. 5H

Picrosirius Red

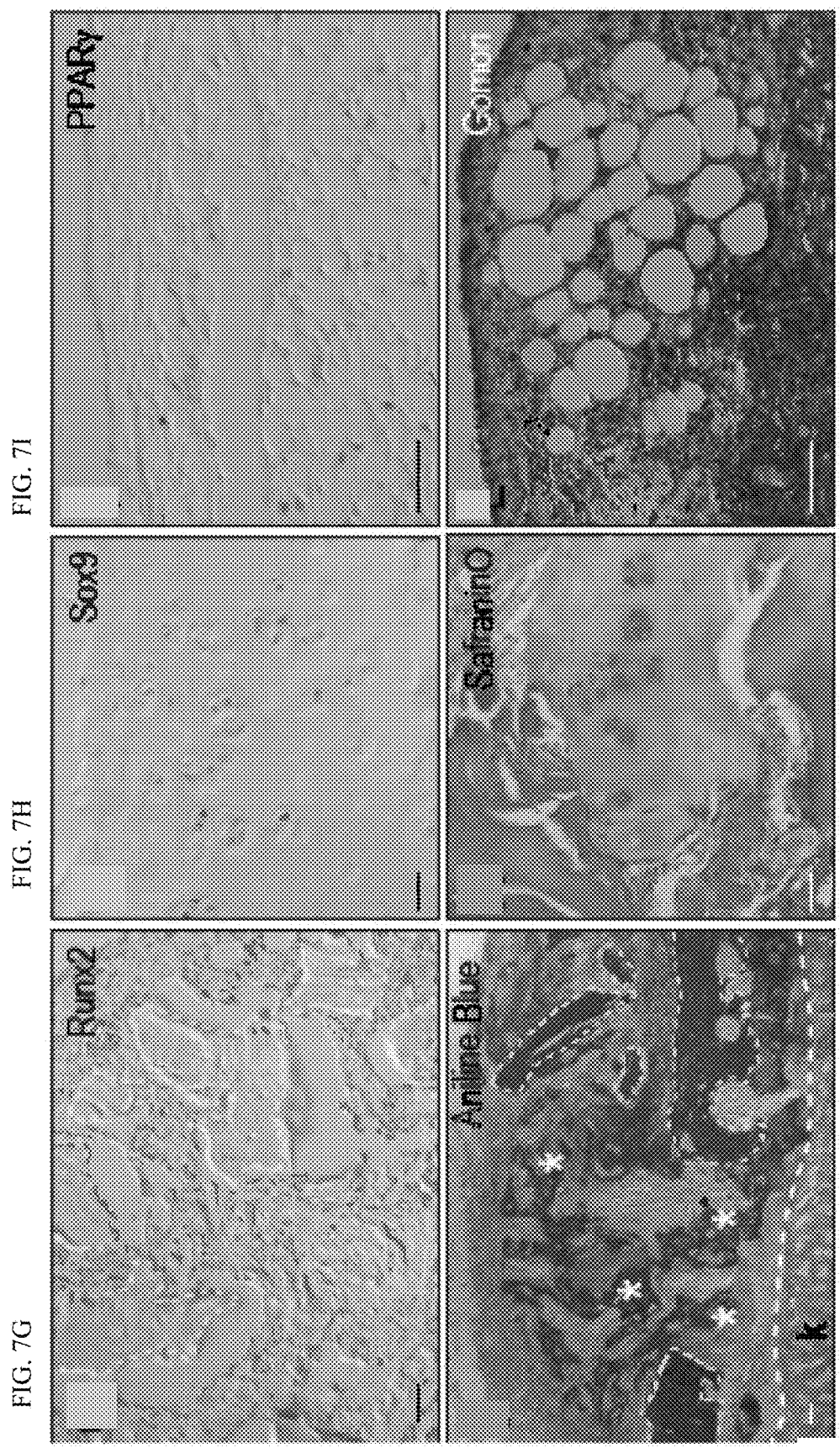

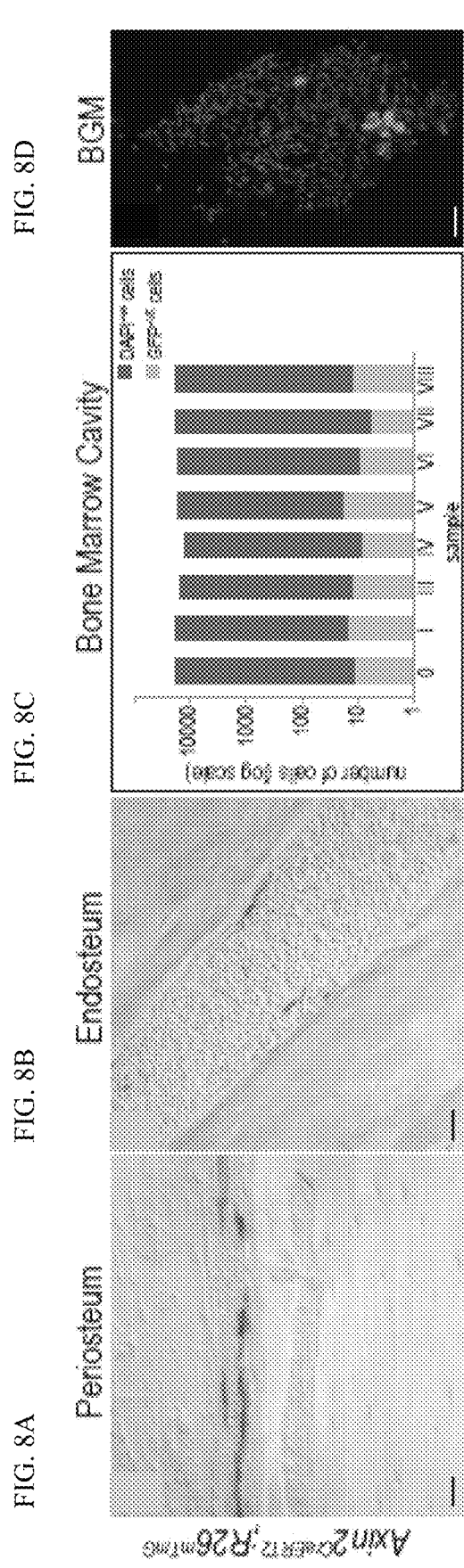
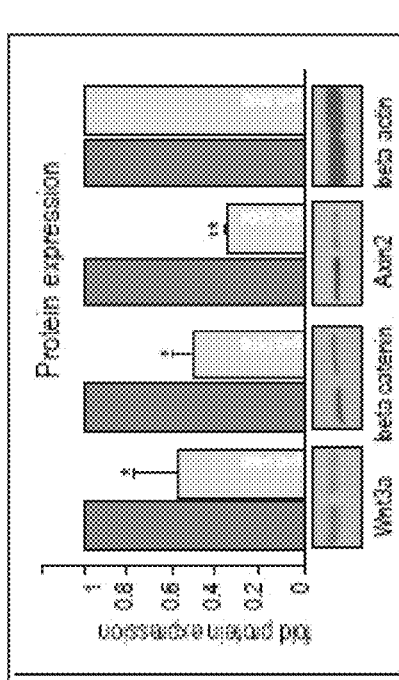
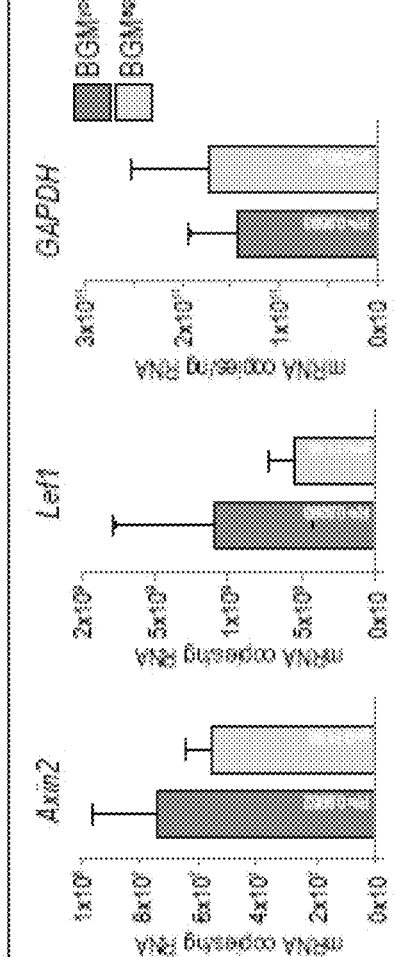
FIG. 8A  FIG. 8B  FIG. 8C  FIG. 8D
FIG. 8E  FIG. 8F

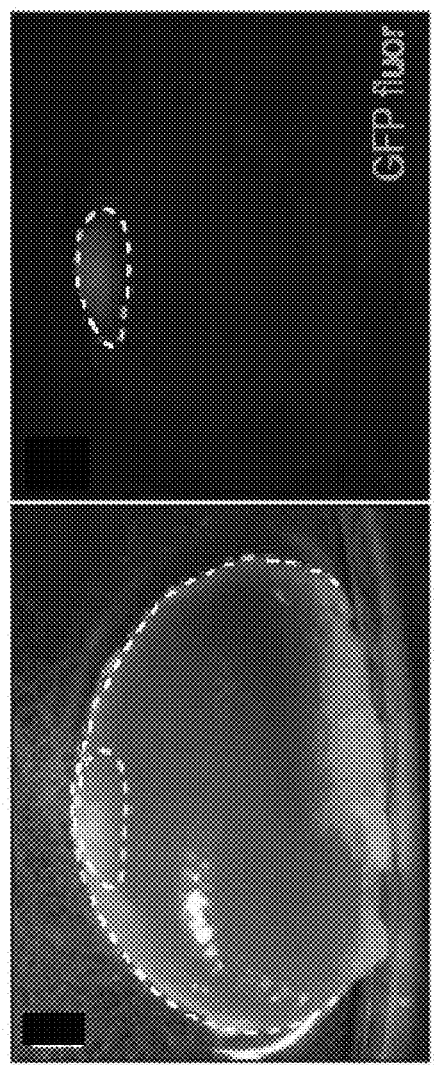
FIG. 9A
FIG. 9B
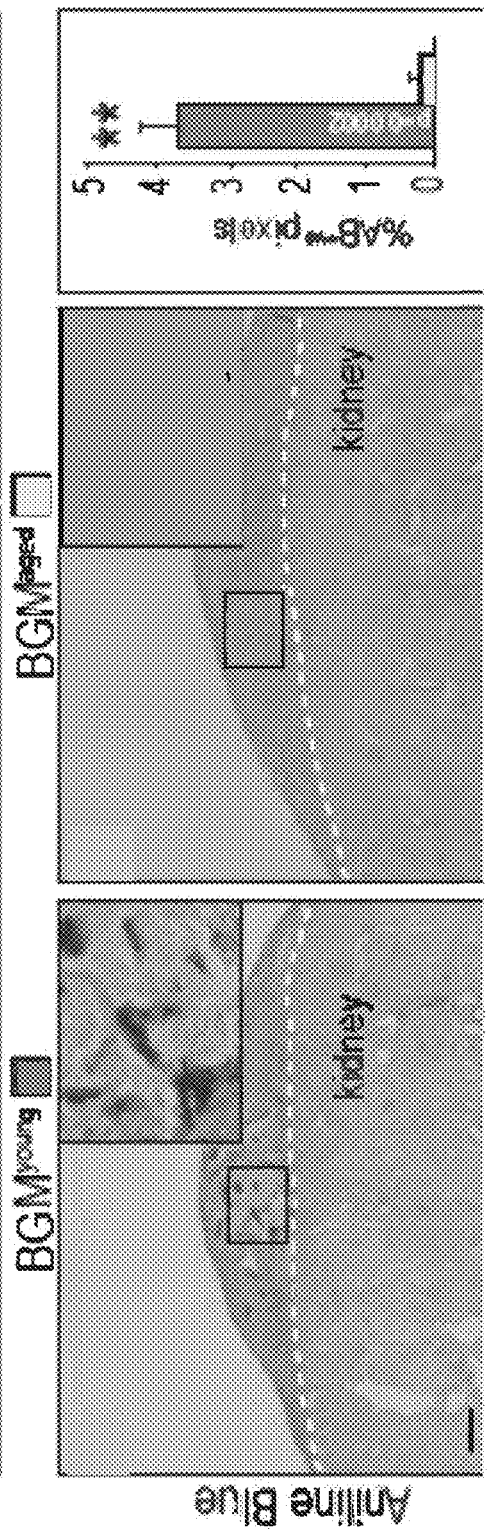
FIG. 9C
FIG. 9D
FIG. 9E
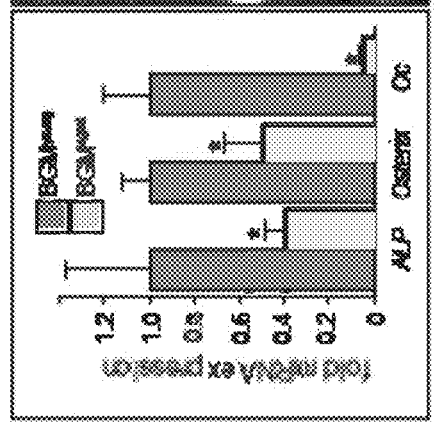
FIG. 9F FIG. 10A
FIG. 10B
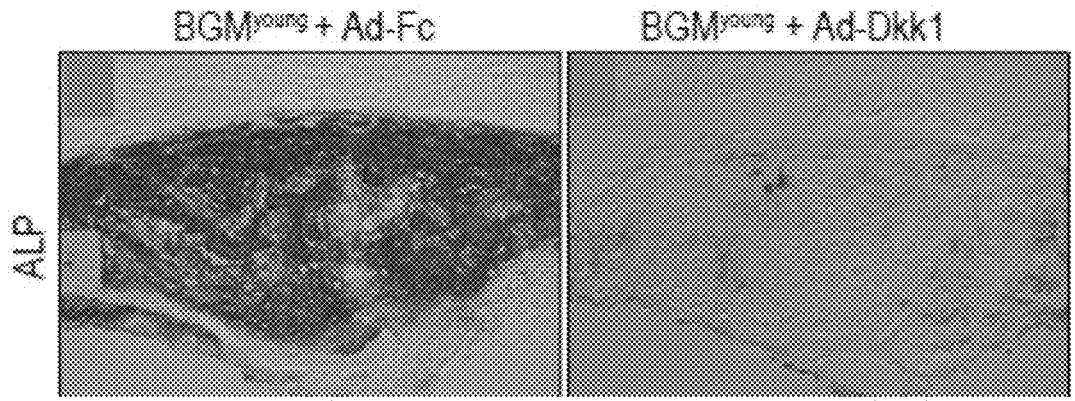
FIG. 10C
FIG. 10D
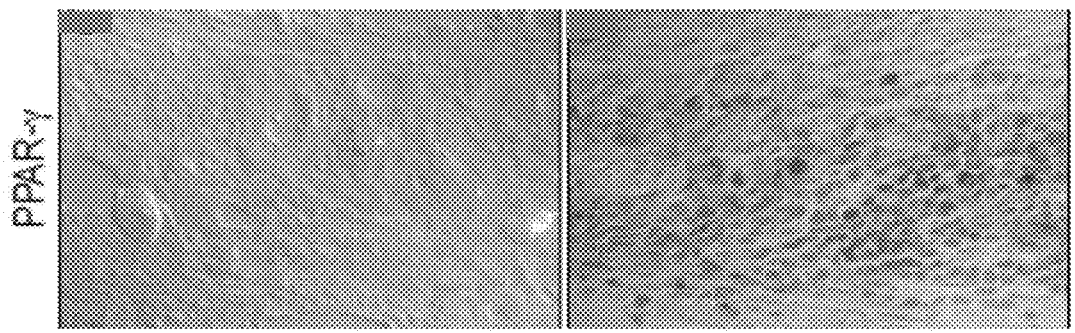
FIG. 10E
FIG. 10F
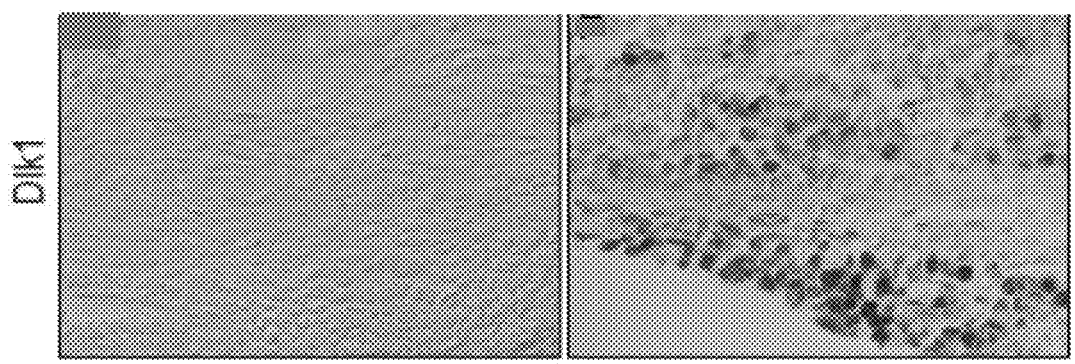

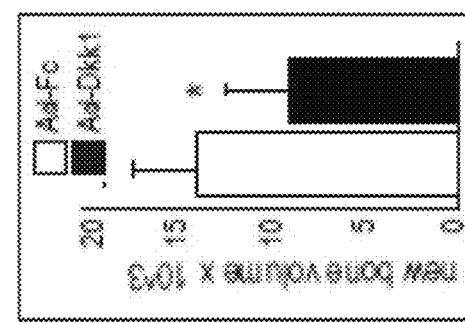
FIG. 10G  FIG. 10H  FIG. 10I
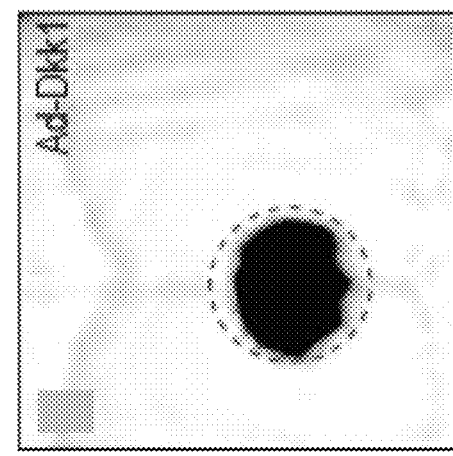
FIG. 10J  FIG. 10K  FIG. 10L

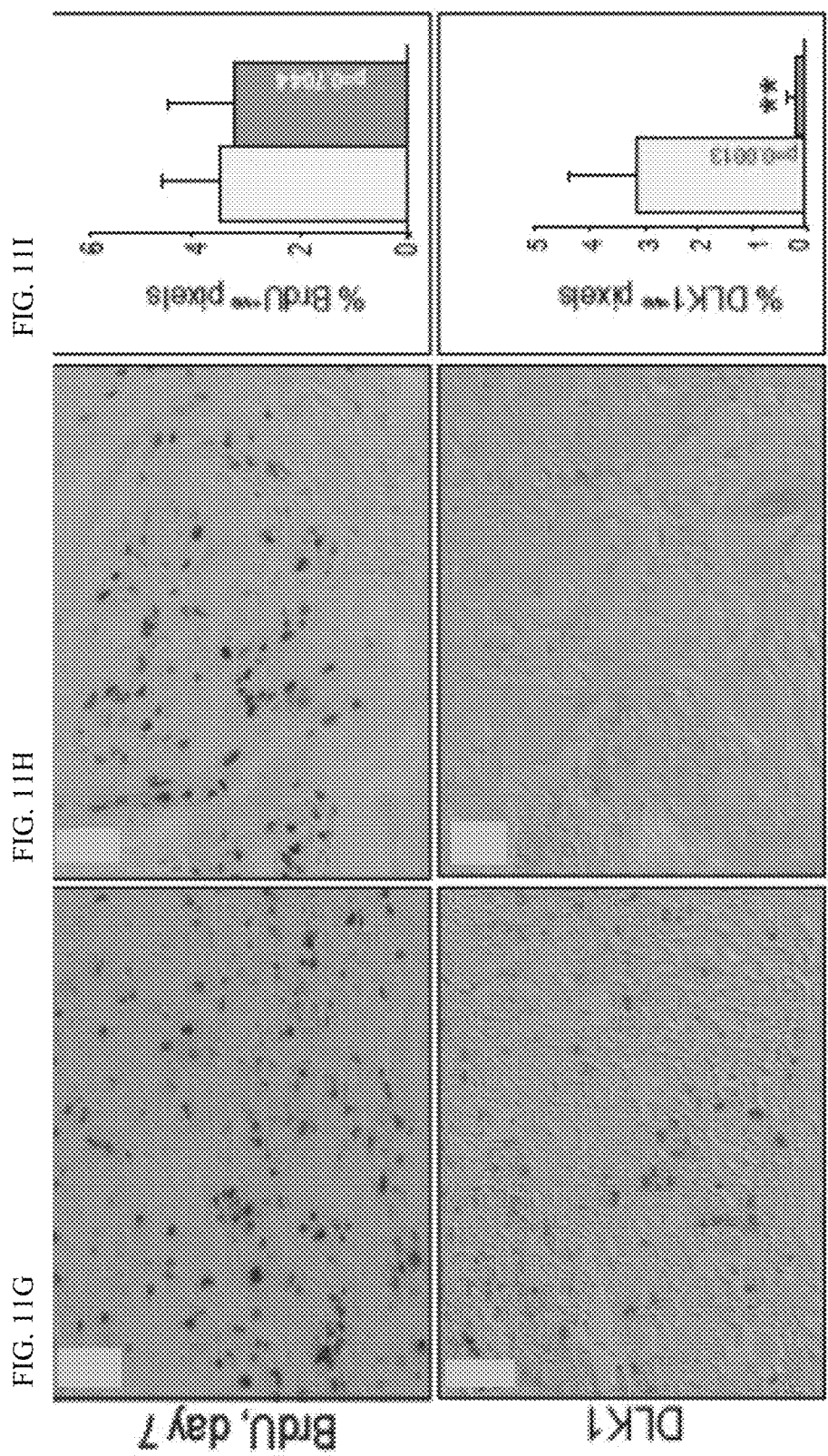

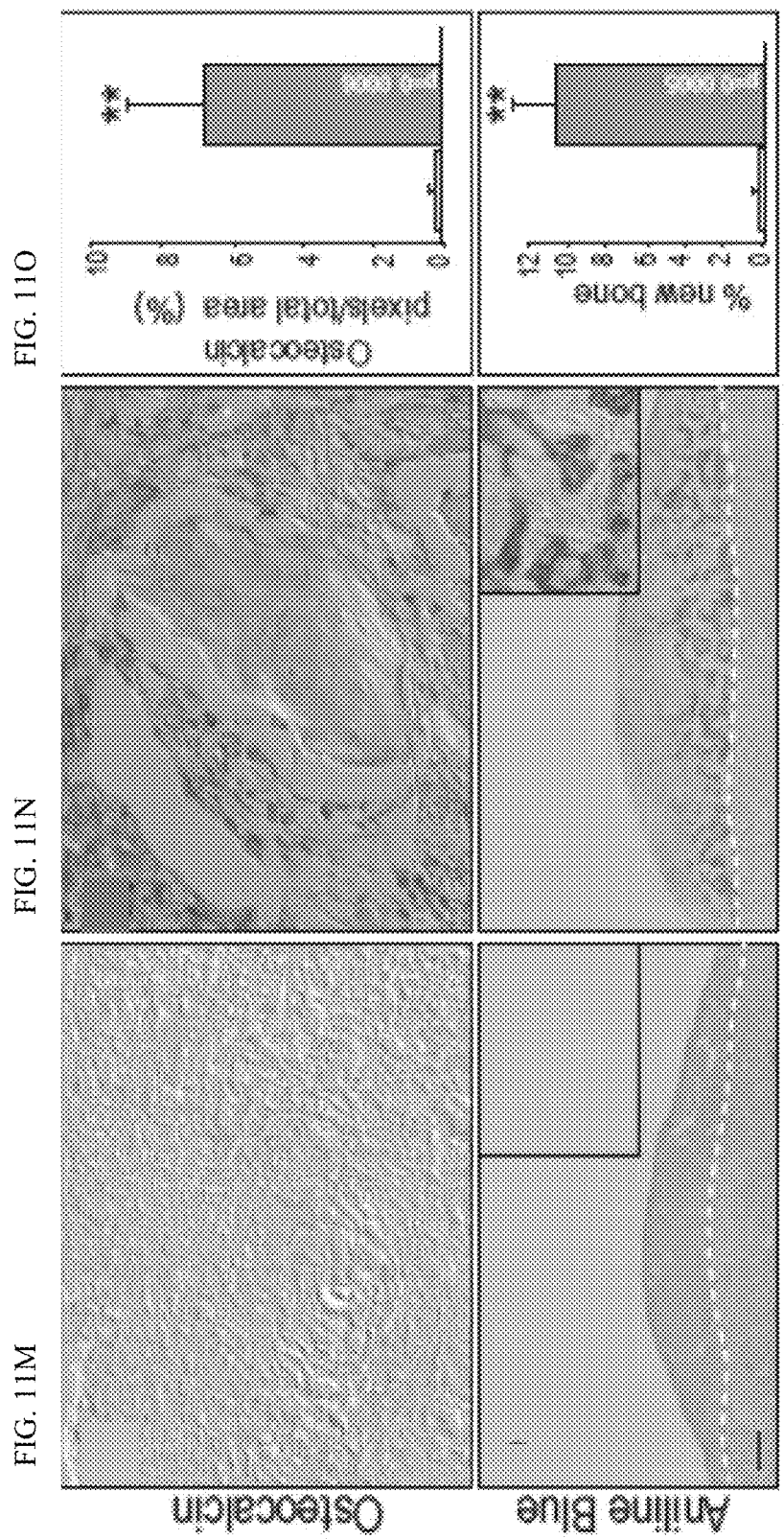

ENHANCEMENT OF OSTEOGENIC POTENTIAL OF BONE GRAFTS

CROSS REFERENCE

This application claims benefit and is a Continuation of Application of Ser. No. 15/868,395 filed Jan. 11, 2018, which is a Continuation of Application of Ser. No. 15/063,317 filed Mar. 7, 2016, which is a Continuation of Application of Ser. No. 14/333,220 filed Jul. 16, 2014, now U.S. Pat. No. 9,301,980, which claims benefit of U.S. Provisional Patent Application No. 61/957,946, filed Jul. 16, 2013, which applications are incorporated herein by reference in their entirety.

FIELD OF THE INVENTION

The present invention concerns the enhancement of the osteogenic potential of bone graft by ex vivo treatment with a Wnt polypeptide, such as a liposomal Wnt polypeptide. In particular, the invention concerns the ex vivo treatment of bone grafts with a Wnt3a protein, preferably liposomal Wnt3a (L-Wnt3a).

BACKGROUND OF THE INVENTION

Orthopedic and dental implants are used for a variety of joint and teeth replacements and to promote bone repair in humans and animals, particularly for hip and knee joint and tooth replacements. Although many individuals experience uncomplicated healing and restoration of function, there is also a high rate of complications, estimated at 10-20% for total joint replacements. The majority of these failures and subsequent revision surgeries are made necessary by failure at the implant-bone interface. In addition, implants used as anchorage devices for orthodontic tooth movement have an estimated 40% failure rate and subsequent placement of additional implants is made necessary because of failures at the implant-bone interface.

Orthopedic and dental implants are made of materials which are relatively inert ("alloplastic" materials), typically a combination of metallic and ceramic or plastic materials. Previous approaches to improve the outcomes of orthopedic implant surgeries have mainly focused on physical changes to the implant surface designed to increased bone formation. These approaches include using implants with porous metallic surfaces to promote bone ingrowth and spraying implants with hydroxyapatite plasma. Approaches using dental implants have also included the use of topographically-enhanced titanium surfaces in which surface roughness is imparted by a method such as grit blasting, acid etching, or oxidation.

Also in an effort to promote osseointegration, implant surfaces have undergone major alterations. For example, short peptides containing an arginine—glycine—aspartic acid (RGD) sequences have been attached to implant surfaces because cells utilize RGD sequences to attach to the extracellular matrix. Investigators have attempted to recreate this cell attachment to the modified implant surface but this strategy has resulted in only modest increases in implant osseointegration and mechanical fixation. Alternatively, in an attempt to stimulate blood vessel ingrowth around implants their surfaces have been coated with a coating containing the angiogenic growth factor VEGF. Implants soaked in saline solutions have been marketed as a means to increase implant osseointegration, with little or no data to substantiate the claims.

Another strategy employed to stimulate osseointegration is to nano-texture the implant surface. The rationale behind this strategy is that texturing increases surface area and therefore prevents the implant from "sliding" against cells in the peri-implant environment. In clinical trials, however, nano-texturing does not result in measureable benefits.

The use of protein-based approaches to stimulate implant osseointegration has also been under intense investigation. Recombinant Bone Morphogenetic Proteins (BMPs) induce robust bone formation in skeletal fractures and they have also been employed in an effort to stimulate direct bone formation around implants. While in vitro results have been encouraging, in vivo data are less convincing. Recombinant BMPs inhibit osteogenic differentiation of cells in the bone marrow cavity and consequently, are contraindicated for implant osseointegration. See Sykaras et al. (2004) Clin Oral Investig 8(4): 196-205; and Minear et al. (2010) Journal of Bone and Mineral Research 25(6): 1196-207. The use of BMPs has been associated with increased incidence of heterotopic ossifications and uncontrolled inflammation and more recent metadata analyses demonstrate an increased risk of cancers as well.

Wnt proteins form a family of highly conserved secreted signaling molecules that bind to cell surface receptors encoded by the Frizzled and low-density lipoprotein receptor related proteins (LRPs). The WNT gene family consists of structurally related genes which encode secreted signaling proteins. These proteins have been implicated in oncogenesis and in several developmental processes, including regulation of cell fate and patterning during embryogenesis. Once bound, the ligands initiate a cascade of intracellular events that eventually lead to the transcription of target genes through the nuclear activity of β-catenin and the DNA binding protein TCF (Clevers H, 2004 Wnt signaling: lg-norrin the dogma. Curr Biol 14: R436-R437; Nelson W J, Nusse R 2004 Convergence of Wnt, beta-catenin, and cadherin pathways. Science 303: 1483-1487; Gordon M D, Nusse 2006 Wnt signaling: Multiple pathways, multiple receptors, and multiple transcription factors. *J Bioi Chem* 281: 22429-22433).

Wnts are also involved in a wide variety of cellular decisions associated with the program of osteogenesis. For example, Wnts regulate the expression levels of sox9 and runx2, which influences the commitment of mesenchymal progenitor cells to a chondrogenic or an osteogenic cell fate. Wnts influence the rate of differentiation of osteoprogenitor cells. In adult animals there is abundant evidence that Wnt signaling regulates bone mass. For example, gain-of-function mutations in the human Wnt co-receptor LRP5 are associated with several high bone mass syndromes, including osteopetrosis type I, and endosteal hyperostosis or autosomal dominant osteosclerosis. Loss-of-Wnt-function mutations cause low bone mass diseases including osteoporosis-pseudoglioma. Increased production of the Wnt inhibitor Dkk1 is associated with multiple myeloma, a disease that has increased bone resorption as one of its distinguishing features. For further details, see, S. Minear et al., Wnt proteins promote bone regeneration. *Sci. Transl. Med.* 2, 29ra30 (2010); Zhao et al., Controlling the in vivo activity of Wnt liposomes, *Methods Enzymol* 465: 331-47 (2009); Popelut et al., The acceleration of implant osseointegration by liposomal Wnt3a, *Biomaterials* 31 9173e9181 (2010); and Morrell N T, Leucht P, Zhao L, Kim J-B, ten Berge D, et al. (2008) Liposomal Packaging Generates Wnt Protein with In Vivo Biological Activity. *PLoS ONE* 3(8): e2930.

It has been shown that combining Wnt proteins with lipid vesicles (liposomes) produced a Wnt formulation (Morrell et al., 2008, supra; and Zhao et al., 2009, supra) with biological activity (Minear et al., 2010, supra; and Popelut et al., 2010, supra). The biological activity of soluble wingless protein is described in van Leeuwen et al. (1994) *Nature* 24: 368 (6469): 3424. Biochemical characterization of Wnt-Frizzled interactions using a soluble, biologically active vertebrate Wnt protein is described by Hsieh et al. (1999) *Proc Natl Acad Sci US A* 96(7): 3546-51. Bradley et al. (1995) *Mol Cell Bioi* 15(8): 4616-22 describe a soluble form of Wnt protein with mitogenic activity. The use of liposomal Wnt proteins to enhance osseointegration is described in U.S. Patent Publication No. 20120115788.

SUMMARY OF THE INVENTION

In one aspect, the invention concerns a method of enhancing cell survival in a bone graft, comprising subjecting the bone graft to ex vivo treatment with a Wnt polypeptide. In another aspect, the invention concerns a method of enhancing the osteogenic potential of a bone graft, comprising subjecting the bone graft to ex vivo treatment with an effective dose of a Wnt polypeptide, including without limitation Wnt3A. In a further aspect, the invention concerns a method for revitalizing a bone graft from a subject with diminished healing potential, comprising subjecting the bone graft to ex vivo treatment with a Wnt polypeptide. In all aspects, the bone graft may be an autograft or an allograft. In all aspects, the bone graft may comprise a stem cell population, such as, for example, a bone-marrow-derived stem cell population, e.g. bone marrow-derived mesenchymal stem cells.

The bone graft preferably is from a human subject. In one embodiment, the human subject is an elderly patient. In certain embodiments, the human subject is at least 50 years old, at least 55 years old, at least 60 years old, or at least 65 years old, or at least 70 years old, or at least 75 years old, or at least 80 years old, or at least 85 years old. In another embodiment, the human subject has diminished healing potential, e.g. is a smoker, diabetic, or a person characterized by nutritional deficits.

In all aspects and embodiments, the Wnt polypeptide preferably is Wnt3a, more preferably human Wnt3a, most preferably liposomal human Wnt3a (L-Wnt3a). In a further aspect, the methods of the present invention further comprise the step of introducing the bone graft into a recipient subject, such as a human patient. In various embodiments, the bone graft may be used to support a dental implant, to repair a bone fracture. In another embodiment, the bone graft is used to repair or rebuild a diseased bone. In yet another embodiment, the bone graft is used in the recipient's hips, knees or spine.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing (s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1J. Bone grafts have osteogenic potential. (FIG. 1A) Quantification of total DNA in representative aliquots of whole bone marrow harvested from transgenic beta actin-enhanced green fluorescent protein (β-actin-eGFP) male mice; each aliquot constitutes a bone graft. (FIG. 1B) Bone grafts are transplanted into 2-mm diameter critical-size calvarial defects (demarcated with a circle), which are created in the sagittal suture that separates the parietal bones (outlined with vertical white dashed lines). The dashed black line indicates the plane of tissue section. (FIG. 1C) Representative tissue section from the injury site on post transplant day 1; GFP immunostaining identifies grafted cells from the eGFP donor (n=5); the inferior space represents the sagittal sinus. (FIG. 1D) Representative tissue section on post-transplant day 5; immunostaining for bromodeoxyuridine (BrdU) identifies cells in S phase. (FIG. 1E) On post transplant day 7, GFP immunostaining identifies the bone graft (dotted yellow line); a higher magnification image of the boxed area in (FIG. 1E) (FIG. 1F) illustrates that the majority of the cells in the injury site are derived from GFP-positive graft. (FIG. 1G) On post-transplant day 14, micro-CT reconstruction confirms that a 2-mm calvarial injury constitutes a critical-size nonhealing defect (n=6)40. (FIG. 1H) The same size calvarial injury, treated with a bone graft, heals (n=6). (FIG. 1I) and (FIG. 1J) On post-transplant day 7, aniline blue staining was used to identify new osteoid matrix; no osteoid matrix formed in the untreated injury site (yellow dotted line). (FIG. 1J) shows visible osteoid matrix on post-transplant day 7 in a representative sample that had been treated with a bone graft. Abbreviations: IHC=immunohistochemistry. Arrows mark the edges of intact bone. Scale bars: 2 mm (FIG. 1B); 200 μm (FIG. 1C) and (FIG. 1D) 100 μm (FIG. 1E); 40 μm (FIG. 1F); 2 mm (FIG. 1G); and 200 μm (FIG. 1I) and (FIG. 1J).

FIG. 2A-2I. Osteogenic potential is reduced in bone grafts from aged animals. On post-transplant day 7 (d7), aniline blue staining indicates osteoid matrix generated by bone grafts from young (FIG. 2A) versus aged donors (FIG. 2B). (FIG. 2C) Histomorphometric analyses of the amount of new bone formed from young and aged bone grafts. (FIG. 2D) On post-transplant day 7 (d7), green fluorescent protein (GFP) immunostaining identifies cells derived from the bone graft when the donor is young as compared with aged donors (FIG. 2E). (FIG. 2F) The number of GFP-positive (GFP$^{+ve}$) cells in the injury site when the graft is harvested from young (blue bars, n=13) compared with aged (white bars, n=13) donors. On post-transplant day 5 (d5), bromodeoxyuridine (BrdU) staining identifies proliferating cells in bone grafts from young (FIG. 2G) and aged (FIG. 2H) donors. (FIG. 2I) Quantitative reverse transcription-polymerase chain reaction (qRTPCR) for proliferating cell nuclear antigen (PCNA) in bone grafts from young and aged animals are equivalent. Single asterisk denotes p<0.05. Arrowmarks the edge of intact bone. Scale bars: 200 μm ((FIG. 2A), [scale bar in (FIG. 2A) also applies to (FIG. 2B)], (FIG. 2D) [scale bar in (FIG. 2D) also applies to FIG. (FIG. 2E)], and (FIG. 2G) [scale bar in FIG. (FIG. 2G) also applies to (FIG. 2H)]).

(FIG. 3A) Quantitative RT-PCR to evaluate relative expression levels of Wnt ligands and Wnt target (FIG. 3B) genes in bone marrow (BM) harvested from young (blue bars; n=3) and aged (white bars; n=3) donors. Gene expression levels normalized to glyceraldehyde 3-phosphate dehydrogenase (GAPDH). Asterisk denotes p<0.05.

(FIG. 4A) Aniline blue staining of L-PBS treated aged bone grafts (n=5). (FIG. 4B) New aniline-blue positive osteoid matrix in L-Wnt3a treated bone grafts (n=8). (FIG. 4C) Histomorphometric quantification of new bone matrix on post-transplant days seven and twelve. (FIG. 4D) Aniline blue staining on post-transplant day twelve (d12) in L-PBS and L-Wnt3a (FIG. 4E) treated bone grafts. (FIG. 4F) Beta galactosidase (β-gal) activity normalized to total DNA as measured in cell populations (unattached, floating cells and attached cells) from a bone marrow harvest. White bars (n=4) represent Wnt responsiveness following L-PBS treatment; blue bars (n=4) represent Wnt responsiveness following L-Wnt3a treatment (effective concentration 0.15 μg/mL Wnt3a). (FIG. 4G) Immunostaining for the stem cell markers CD45, CD73, CD105, and Stro1 in attached cells derived from the bone marrow. (FIG. 4H) Beta galactosidase activity normalized to total DNA in the attached cell population following L-PBS treatment (white bars, n=4) or following L-Wnt3a treatment (n=4; effective concentration 0.15 μg/mL Wnt3a). (FIG. 4I) Xgal staining on a representative tissue section identifies Wnt responsive cells in a bone graft from an aged $Axin2^{LacZ/+}$ mouse treated with L-PBS, compared with treatment with L-Wnt3a (FIG. 4J). (FIG. 4K) Xgal staining on a representative tissue section identifies Wnt responsive cells in an L-PBS-treated bone graft from a young $Axin2^{LacZ/+}$ mouse. Single asterisk denotes $p<0.05$; quadruple asterisk denotes $p<0.0001$. Abbreviations: L-PBS=liposomal PBS; L-Wnt3a=liposomal Wnt3a; BM=bone marrow; and DAPI=4', 6-diamidino-2-phenylindole, dihydrochloride. Arrows mark the edges of intact bone. Scale bars: 100 mm ((FIG. 4A) [scale bar in (FIG. 4A) also applies to (FIG. 4B)]); 200 mm ((FIG. 4D) [scale bar in (FIG. 4D) also applies to (FIG. 4E)]); 100 mm (FIG. 4G); and 40 mm ((FIG. 4I), [scale bar in (FIG. 4I) also applies to (FIG. 4J) and (FIG. 4K)]).

FIG. 5A-5H. L-Wnt3a treatment restores osteogenic potential to bone grafts from aged animals. Bone marrow from aged donor rabbits, assayed for DNA fragmentation associated with cell apoptosis. (FIG. 5A) Terminal deoxynucleotidyl transferase dUTP nick end labeling (TUNEL) staining (n=4) demonstrates the extent of apoptosis in aged bone marrow treated with L-PBS (10 mL), compared with L-Wnt3a (FIG. 5B) treatment (effective concentration=0.15 μg/mL Wnt3a). (FIG. 5C) A measurement of caspase activity in aged bone graft samples treated with L-PBS (white bars) or L-Wnt3a (blue bars). (FIG. 5D) through (FIG. 5G) Bone marrow was harvested from aged rabbits, incubated in L-PBS or L-Wnt3a for up to 1 h, then transplanted into a critical-size defect created in the ulna. (FIG. 5D) Radiographic assessment at four weeks following bone-grafting. Compare L-PBS treatment with L-Wnt3a (FIG. 5E) treatment. (FIG. 5F) Micro-CT iso-surface reconstruction at eight weeks following bone-grafting. Compare L-PBS treatment with L-Wnt3a (FIG. 5G) treatment. (FIG. 5H) Bone volume (BV) and bone volume/total volume (BV/TV) are calculated using the bone analysis tool in GE MicroView software. A single asterisk denotes $p<0.05$. Abbreviations: L-PBS=liposomal PBS and L-Wnt3a=liposomalWnt3a. Arrows mark the edge of intact bone. Scale bars: 40 mm (FIG. 5A) and (FIG. 5B); and 5 mm (FIG. 5F) and (FIG. 5G).

(FIG. 6C) Gomori trichrome staining of aged host's fatty bone marrow cavity, and the adjacent injury (FIG. 6D) area that received an L-PBS treated aged bone graft; fibrous tissue is stained turquoise blue. (FIG. 6E) Gomori trichrome staining of aged host's fatty bone-marrow cavity, and the adjacent injury (FIG. 6F) area that received an L-PBS treated aged bone graft; mature osteoid matrix stains dark turquoise and osteocyte nuclei stain red. (FIG. 6G) Under polarized light, picrosirius red staining identifies fibrous tissue that has formed from aged bone graft treated with L-PBS. Compare with the osteoid matrix (FIG. 6H) that has formed from aged bone graft treated with L-Wnt3a. Abbreviations: L-PBS=liposomal PBS, and L-Wnt3a=liposomal Wnt3a. Arrows mark the edge of intact bone. Scale bars: 500 μm (FIG. 6A) and (FIG. 6B); 100 μm (FIG. 6C) through (FIG. 6F); and 200 μm (FIG. 6G) and (FIG. 6H).

FIG. 7A-7L. Bone graft material contains stem and progenitor cell populations. (FIG. 7A) Gomori staining of BGM harvested from rat femur, (FIG. 7B) the iliac crest, and (FIG. 7C) the tibia. (FIG. 7D) Quantitative RTPCR analyses of endogenous osteogenic gene expression in freshly harvested rat BGM from the indicated sources. (FIG. 7E) Schematic of experimental design, where autologous BGM is transplanted into the SRC of rats. (FIG. 7F) Representative tissue sections of iliac crest BGM on post-transplant day 7, stained to detect BrdU incorporation. Dotted lines indicate trabecular bone chips included in the BGM. (FIG. 7G) Runx2, (FIG. 7H) Sox9, and (FIG. 7I) PPARγ expression. (FIG. 7J) Representative tissue sections of BGM stained with Aniline blue to detect osteoid matrix; asterisks indicate new bone matrix as opposed to old bone chips (yellow dotted line). The kidney surface is indicated with a dotted white line in this panel, and in G. (FIG. 7K) Safranin O/Fast green histology to detect proteoglycan-rich cartilage (red), and (FIG. 7L) Gomori trichrome staining to detect adipocytes. Abbreviations: BrdU, bromodeoxyuridine; PPARγ, peroxisome proliferator-activated protein gamma. Scale bars: 50 μm, asterisks: $p<0.05$.

FIG. 8A-8F. Bone graft material is Wnt responsive (FIG. 8A) GFP+ve cells in $Axin2^{CreERT2}$; R26 m$^{TmG}$ mice, visualized by immunostaining of the periosteum and (FIG. 8B) endosteum. (FIG. 8C) Quantification of GFP$^{+ve}$ cells/total cells within specified microscopic fields of view. (FIG. 8D) GFP$^{+ve}$ cells in the BGM were visualized by fluorescence. (FIG. 8E) Quantitative absolute RT-PCR results for endogenous Axin2, Lef1, and GAPDH expression in BGM$^{young}$ (green bars) and BGM$^{aged}$ (grey bars). (FIG. 8F) Western blot analyses for Wnt3a, total beta catenin, Axin2, and beta actin in in BGM$^{young}$(green bars) and BGM$^{aged}$ (grey bars). Scale bars=50 μm. Asterisks: $p<0.05$.

FIG. 9A-9L. The osteogenic differentiation potential of BGM declines with age. (FIG. 9A) Quantitative RT-PCR analyses for expression of alkaline phosphatase, Osterix, and Osteocalcin in BGM$^{young}$ (green bars) and BGM$^{aged}$ (grey bars). (FIG. 9B) BGM harvested from ACTB-eGFP mice, transplanted into the SRC and visualized under brightfield and (FIG. 9C) fluorescent light to detect the GFP signal in BGM. (FIG. 9D) Representative tissue sections stained with Aniline blue (inset) from BGM$^{young}$ (N=5) and (FIG. 9E) BGM$^{aged}$ (N=5). Dotted line indicates the kidney surface. (FIG. 9F) Histomorphometric analyses of Aniline blue$^{+ve}$ pixels within the total area occupied by the BGM on post-transplant day 7. (FIG. 9G) Representative tissue sections stained to detect ALP activity from BGM$^{young}$ (N=5) and (FIG. 9H) BGM$^{aged}$ (N=5). (FIG. 9I) Quantification of ALP$^{+ve}$ pixels within the total area occupied by the BGM on post-transplant day 7. (FIG. 9J) Representative tissue sections immunostained for GFP from BGM$^{young}$ (N=5) and (FIG. 9K) BGM$^{aged}$ (N=5). (FIG. 9L) Quantification of GFP$^{+ve}$ pixels within the total area occupied by the BGM on post-transplant day 7. Abbreviations: ALP, alkaline phosphatase; Oc, Osteocalcin. Scale bars: 100 μm. Asterisks: $p<0.05$; double asterisks: $p<0.01$.

FIG. 10A-10L. Osteogenic differentiation of BGM requires an endogenous Wnt signal. (FIG. 10A) Representative tissue sections stained for ALP activity in BGM treated with the murine IgG2α Fc fragment (Ad-Fc) or (FIG. 10B) adenovirus expressing the soluble Wnt antagonist Dkk1 (Ad-Dkk1). (FIG. 10C) Representative tissue sections immunostained for PPARγ in BGM treated with Ad-Fc or (FIG. 10D) Ad-Dkk1. (FIG. 10E) Representative tissue sections immunostained for Dlk1 in BGM treated with Ad-Fc or (FIG. 10F) Ad-Dkk1. (FIG. 10G) Micro-CT reconstruction to detect bone formation in defect sites that received BGM treated with Ad-Fc or (FIG. 10H) Ad-Dkk1. Original defect is indicated with a dotted red circle. (FIG. 10I) New bone volume (N=5) calculated from micro-CT data±SEM. (FIG. 10J) Aniline blue staining on representative tissue sections from defect sites that received BGM treated with Ad-Fc or (FIG. 10K) Ad-Dkk1. (FIG. 10L) Quantification of new bone volume using histomorphometric analyses (see Methods). (FIG. 10I) PPAR-γ expression in BM grafts treated with Ad-Fc or (FIG. 10J) Ad-Dkk1. Single asterisk p<0.05. Scale bars: A-B, 200 m, CF, J-K, 50 m, G-H, 2 mm.

FIG. 11A-11R. Wnt3a activates BGM$^{aged}$ and restores its osteogenic differentiation potential. (FIG. 11A) BGMs from aged ACTB-eGFP mice, treated with L-PBS or L-WNT3A (0.15 μg/ml) for 1 h then either assayed by qRT-PCR for target gene expression 24 h later, or immediately transplanted into the SRC for 7 days. (FIG. 11B) Fold change in Axin2 and Lef1 expression in BGM$^{aged}$ treated with either L-PBS (grey bars) or L-WNT3A (blue bars). (FIG. 11C) Western blot analysis of total beta catenin, Axin2, and beta actin in BGM$^{aged}$ treated with either L-PBS (grey bars) or L-WNT3A (blue bars). After harvesting BGM$^{aged}$ from the SRC on post-transplant day 4, representative tissue sections from (FIG. 11D) L-PBS (N=5) and (FIG. 11E) L-WNT3A were stained for BrdU incorporation (N=5). (FIG. 11F) Quantification of BrdU$^{+ve}$ pixels within a microscopic field of view centered in the middle of the bone grafts. (FIG. 11G) Representative tissue sections from L-PBS (N=5) and (FIG. 11H) L-WNT3A treated (N=5) samples, stained for BrdU incorporation on post-transplant day 7. (FIG. 11I) Quantification of BrdU+ve pixels as above. (FIG. 11J) Representative tissue sections from L-PBS (N=5) and (FIG. 11K) L-WNT3A treated (N=5) samples, immunostained for Dlk1 expression on post-transplant day 7. (FIG. 11L) Quantification of Dlk1+ve pixels within the total area occupied by the BGM on post-transplant day 7. (FIG. 11M) Representative tissue sections from L-PBS (N=5) and (FIG. 11N) L-WNT3A treated (N=5) samples, immunostained for Oc expression on post-transplant day 7. (FIG. 11O) Quantification of Oc$^{+ve}$ pixels as described for Dlk1. (FIG. 11P) Representative tissue sections stained with Aniline blue to detect osteoid matrix in L-PBS (N=5) and (FIG. 11Q) LWNT3A treated (N=5) samples. (FIG. 11R) Histomorphometric quantification of new bone matrix; see Methods for details. Abbreviations as in previous figure legends. Scale bars: 100 μm. Asterisks: p<0.05; double asterisks: p<0.01.

(FIG. 12B) Murine SSC were treated with L-PBS or LWNT3A for 12 h at 37° C. and Wnt response was assayed with qRT-PCR for Axin2 expression. (FIG. 12C) Quantitative absolute RT-PCR analyses for Axin2 and Lef1 expression in response to 1 h incubation at room temperature with L-PBS (dashed line) or L-WNT3A (0.15 μg/mL; blue line). Data is expressed as a ratio of RNA copies/total RNA content over a 24 h period. (FIG. 12D) Rat spinous processes were exposed via minimal incisions and standardized volumes of autologous BGM from the iliac crest were treated with L-PBS or L-WNT3A for 1 hr then (FIG. 12E) transplanted between the transverses processes of the L4 and L5 vertebrae. (FIG. 12F) At POD2 Micro-CT acquisitions were performed for graphs (pink) treated with L-PBS and (FIG. 12G) L-WNT3A. (FIG. 12H) At POD49 Micro-CT acquisitions were again performed to evaluate the bone growth of the transplants treated with L-PBS (gray) and (FIG. 12I) L-WNT3A (blue). (FIG. 12J) Transplant growth was graphed for each of the treatment groups as fold volume, comparing each graft size on POD2 to its size on POD49 (indicated by the colors stated above). Abbreviations: L4, Lumbar #4, L5, Lumbar #5, AP, apical process, SP, spinous process, TP, transverse process, POD, postoperation day.

DETAILED DESCRIPTION OF THE INVENTION

Definitions

Figure 1E:
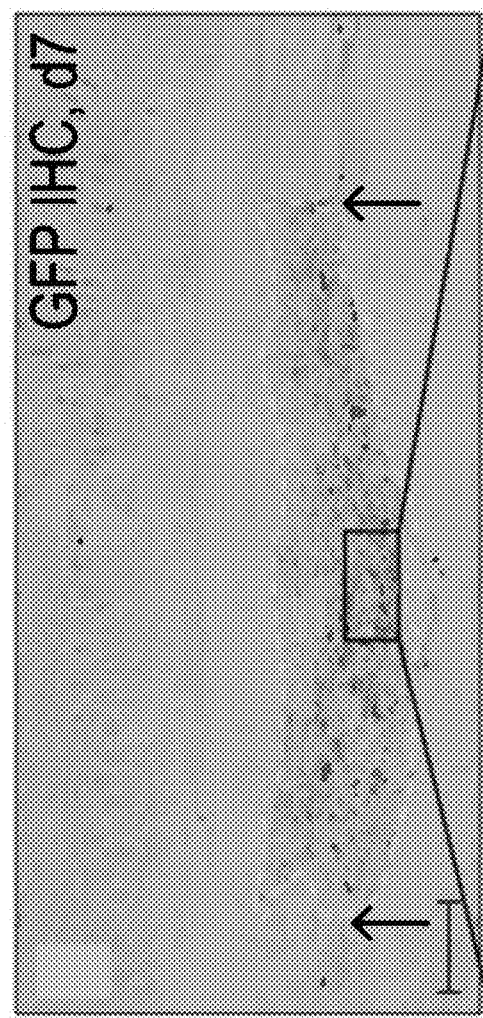
Figure 1F:
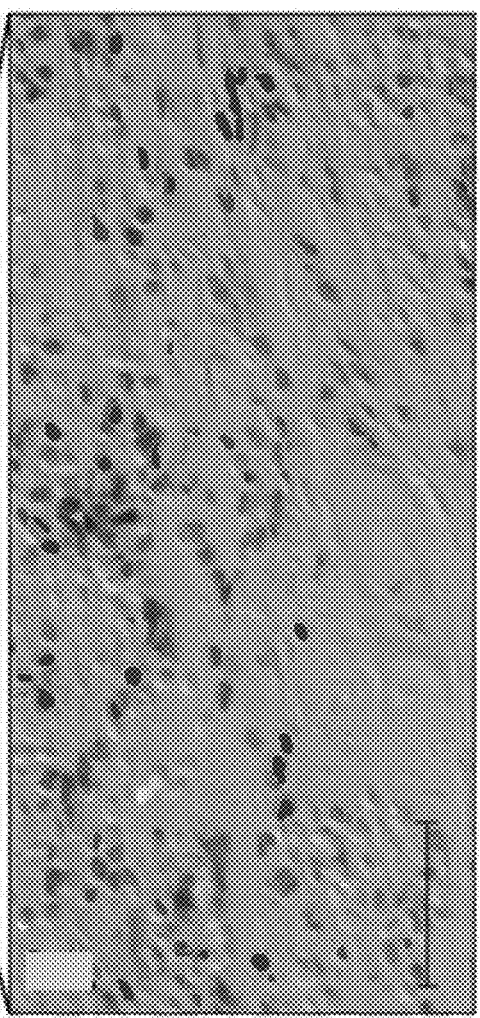
Figure 1G:
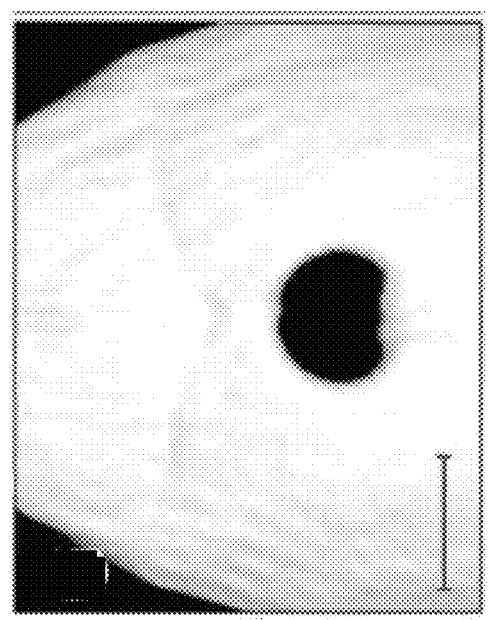
Figure 1H:

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range. Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), provides one skilled in the art with a general guide to many of the terms used in the present application.

All publications mentioned herein are expressly incorporated herein by reference to disclose and describe the methods and/or materials in connection with which the publications are cited.

Wnt protein. Wnt proteins form a family of highly conserved secreted signaling molecules that regulate cell-to-cell interactions during embryogenesis. The terms "Wnts" or "Wnt gene product" or "Wnt protein" or "Wnt polypeptide" are used interchangeable and encompass native sequence Wnt polypeptides, Wnt polypeptide variants, Wnt polypeptide fragments and chimeric Wnt polypeptides. In some embodiments of the invention, the Wnt protein comprises palmitate covalently bound to a cysteine residue. A "native sequence" polypeptide is one that has the same amino acid sequence as a Wnt polypeptide derived from nature, regardless of the method used for its production. Such native sequence polypeptides can be isolated from cells producing endogenous Wnt protein or can be produced by recombinant or synthetic means. Thus, a native sequence polypeptide can have the amino acid sequence of, e.g. naturally occurring human polypeptide, murine polypeptide, or polypeptide from any other mammalian species, or from non-mammalian species, e.g. *Drosophila, C. elegans*, and the like.

The term "native sequence Wnt polypeptide" includes, without limitation, human and murine Wnt polypeptides. Human Wnt proteins include the following: Wnt1, Genbank reference NP005421.1; Wnt2, Genbank reference NP003382.1, which is expressed in brain in the thalamus, in fetal and adult lung and in placenta; two isoforms of Wnt2B, Genbank references NP004176.2 and NP078613.1. Isoform 1 is expressed in adult heart, brain, placenta, lung, prostate, testis, ovary, small intestine and colon. In the adult brain, it is mainly found in the caudate nucleus, subthalamic nucleus and thalamus. Also detected in fetal brain, lung and kidney. Isoform 2 is expressed in fetal brain, fetal lung, fetal kidney, caudate nucleus, testis and cancer cell lines. Wnt 3 and Wnt3A play distinct roles in cell-cell signaling during morphogenesis of the developing neural tube, and have the Genbank references NP11 0380.1 and X56842 (Swiss-Prot P56704), respectively.

The native human Wnt3A amino acid and nucleotide sequences are specifically disclosed as SEQ ID NOs: 1 and 2, respectively. Wnt3A is expressed in bone marrow. Wnt 4 has the Genbank reference NP11 0388.2. Wnt 5A and Wnt 5B have the Genbank references NP003383.1 and AK013218. Wnt 6 has the Genbank reference NP006513.1; Wnt 7A is expressed in placenta, kidney, testis, uterus, fetal lung, and fetal and adult brain, Genbank reference NP004616.2. Wnt 7B is moderately expressed in fetal brain, weakly expressed in fetal lung and kidney, and faintly expressed in adult brain, lung and prostate, Genbank reference NP478679.1. Wnt 8A has two alternative transcripts, Genbank references NP114139.1 and NP490645.1. Wnt 8B is expressed in the forebrain, and has the Genbank reference NP003384.1. Wnt 10A has the Genbank reference NP079492.2. Wnt 10B is detected in most adult tissues, with highest levels in heart and skeletal muscle. It has the Genbank reference NP003385.2. Wnt 11 is expressed in fetal lung, kidney, adult heart, liver, skeletal muscle, and pancreas, and has the Genbank reference NP004617 0.2. Wnt 14 has the Genbank reference NP003386.1. Wnt 15 is moderately expressed in fetal kidney and adult kidney, and is also found in brain. It has the Genbank reference NP003387.1. Wnt 16 has two isoforms, Wnt-16a and Wnt-16b, produced by alternative splicing. Isoform Wnt-16B is expressed in peripheral lymphoid organs such as spleen, appendix, and lymph nodes, in kidney but not in bone marrow. Isoform Wnt-16a is expressed at significant levels only in the pancreas. The Genbank references are NP057171.2 and NP476509.1. All GenBank, SwissProt and other database sequences listed are expressly incorporated by reference herein.

The term "native sequence Wnt protein" or "native sequence Wnt polypeptide" includes the native proteins with or without the initiating N-terminal methionine (Met), and with or without the native signal sequence. The terms specifically include the 352 amino acids long native human Wnt3a polypeptide, without or without its N terminal methionine (Met), and with or without the native signal sequence.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active Wnt variant will have an amino acid sequence having at least about 90% amino acid sequence identity with a native sequence Wnt polypeptide, preferably at least about 95%, more preferably at least about 99%.

A "chimeric" Wnt polypeptide is a polypeptide comprising a Wnt polypeptide or portion (e.g., one or more domains) thereof fused or bonded to heterologous polypeptide. The chimeric Wnt polypeptide will generally share at least one biological property in common with a native sequence Wnt polypeptide. Examples of chimeric polypeptides include immunoadhesins, combine a portion of the Wnt polypeptide with an immunoglobulin sequence, and epitope tagged polypeptides, which comprise a Wnt polypeptide or portion thereof fused to a "tag polypeptide". The tag polypeptide has enough residues to provide an epitope against which an antibody can be made, yet is short enough such that it does not interfere with biological activity of the Wnt polypeptide. Suitable tag polypeptides generally have at least six amino acid residues and usually between about 6-60 amino acid residues.

A "functional derivative" of a native sequence Wnt polypeptide is a compound having a qualitative biological property in common with a native sequence Wnt polypeptide. "Functional derivatives" include, but are not limited to, fragments of a native sequence and derivatives of a native sequence Wnt polypeptide and its fragments, provided that they have a biological activity in common with a corresponding native sequence Wnt polypeptide. The term "derivative" encompasses both amino acid sequence variants of Wnt polypeptide and covalent modifications thereof.

Biologically Active Wnt. The methods of the present invention provide for Wnt compositions that are active when administered to an animal, e.g. a mammal, such as a human, in vivo. One may determine the specific activity of a Wnt protein in a composition by determining the level of activity in a functional assay, for example in an in vitro assay, or after in vivo administration in a test model, e.g. accelerating bone regeneration, upregulation of stem cell proliferation, etc., quantitating the amount of Wnt protein present in a non-functional assay, e.g. immunostaining, ELISA, quantitation on Coomasie or silver stained gel, etc., and determining the ratio of in vivo biologically active Wnt to total Wnt.

Lipid Structure. As used in the methods of the invention, lipid structures are found to be important in maintaining the activity of Wnt proteins following in vivo administration. The Wnt proteins are not encapsulated in the aqueous phase of these structures, but are rather integrated into the lipid membrane, and may be inserted in the outer layer of a membrane. Such a structure is not predicted from conventional methods of formulating proteins in, for example, liposomes. A Wnt polypeptide with such lipid structure is referred herein as L-Wnt, such as L-Wnt3a. The methods used for tethering Wnt proteins to the external surface of a liposome or micelle may utilize a sequence so as to emphasize the exoliposomal display of the protein, where crude liposomes are first pre-formed; Wnt protein is then added to the crude mixture, which will favor addition of exo-liposomal Wnt, followed by various formulation steps, which may include size filtering; dialysis, and the like. Suitable lipids include fatty acids, neutral fats such as triacylglycerols, fatty acid esters and soaps, long chain (fatty) alcohols and waxes, sphingoids and other long chain bases, glycolipids, sphingolipids, carotenes, polyprenols, sterols, and the like, as well as terpenes and isoprenoids. For example, molecules such as diacetylene phospholipids may find use. Included are cationic molecules, including lipids, synthetic lipids and lipid analogs, having hydrophobic and hydrophilic moieties, a net positive charge, and which by itself can form spontaneously into bilayer vesicles or micelles in water. Liposomes manufactured with a neutral charge, e.g. DMPC, are preferred. The term also includes any amphipathic molecules that can be stably incorporated into lipid micelle or bilayers in combination with phospholipids, with its hydrophobic moiety in contact with the interior, hydrophobic region of the micelle or bilayer membrane, and its polar head group moiety oriented toward the exterior, polar surface of the membrane.

The term "cationic amphipathic molecules" is intended to encompass molecules that are positively charged at physiological pH, and more particularly, constitutively positively charged molecules, comprising, for example, a quaternary ammonium salt moiety. Cationic amphipathic molecules typically consist of a hydrophilic polar head group and lipophilic aliphatic chains. Similarly, cholesterol derivatives having a cationic polar head group may also be useful. See, for example, Farhood et al. (1992) Biochim. Biophys. Acta 1111:239-246; Vigneron et al. (1996) Proc. Natl. Acad. Sci. (USA) 93:9682-9686. Cationic amphipathic molecules of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include DOTIM (also called BODAI) (Saladin et al., (1995) Biochem. 34: 13537-13544), DDAB (Rose et al., (1991) BioTechniques 10(4):520-525), DOTMA (U.S. Pat. No. 5,550,289), DOTAP (Eibl and Wooley (1979) Biophys. Chern. 10:261-271), DMRIE (Feigner et al., (1994) J. Bioi. Chern. 269(4): 2550-2561), EDMPC (commercially available from Avanti Polar Lipids, Alabaster, Ala.), DCC hoi (Gau and Huang (1991) Biochem. Biophys. Res. Comm. 179:280-285), DOGS (Behr et al., (1989) Proc. Nat!. Acad. Sci. USA, 86:6982-6986), MBOP (also called MeBOP) (WO 95/14651), and those described in WO 97/00241.

While not required for activity, in some embodiments a lipid structure may include a targeting group, e.g. a targeting moiety covalently or non-covalently bound to the hydrophilic head group. Head groups useful to bind to targeting moieties include, for example, biotin, amines, cyano, carboxylic acids, isothiocyanates, thiols, disulfides, ahalocarbonyl compounds, a,p-unsaturated carbonyl compounds, alkyl hydrazines, etc. Chemical groups that find use in linking a targeting moiety to an amphipathic molecule also include carbamate; amide (amine plus carboxylic acid); ester (alcohol plus carboxylic acid), thioether (haloalkane plus sulfhydryl; maleimide plus sulfhydryl), Schiffs base (amine plus aldehyde), urea (amine plus isocyanate), thiourea (amine plus isothiocyanate), sulfonamide (amine plus sulfonyl chloride), disulfide; hyrodrazone, lipids, and the like, as known in the art. For example, targeting molecules may be formed by converting a commercially available lipid, such as DAGPE, a PEG-PDA amine, DOTAP, etc. into an isocyanate, followed by treatment with triethylene glycol diamine spacer to produce the amine terminated thiocarbamate lipid which by treatment with the para-isothiocyanophenyl glycoside of the targeting moiety produces the desired targeting glycolipids. This synthesis provides a water soluble flexible linker molecule spaced between the amphipathic molecule that is integrated into the nanoparticle, and the ligand that binds to cell surface receptors, allowing the ligand to be readily accessible to the protein receptors on the cell surfaces. Further information about liposomal Wnt compositions and their use is found in U.S. Application Publication 20120115788.

The term "bone graft" is used herein in the broadest sense and specifically includes autografts and allografts, harvested from the patient's own bones or from an individual other than the one receiving the graft, including cadavers, respectively. The term "bone graft" also includes autologous or allogeneic pluripotent stem cell populations, e.g. stem cells harvested from bone marrow, e.g. bone marrow-derived mesenchymal stem cells. Bone grafts can be obtained from a donor by various means, including without limitation reamer, irrigation, aspirator methods.

DETAILED DESCRIPTION OF THE EMBODIMENTS

Osteogenic competence is enhanced by incubating cells for a bone graft with an effective dose of a Wnt protein, e.g. L-Wnt3A, for a period of time sufficient to enhance osteogenic potential.

The bone graft material, as used herein, refers to a cellular composition obtained from a donor, which donor may be living or cadaveric. Bone graft material typically comprises complex cell populations, and includes stem cells such as mesenchymal stem cells, and may also comprise osteocytes and progenitors thereof. The donor may be allogeneic or autologous relative to the recipient. The quantity of cells for a bone graft may vary with the donor, the recipient, purpose of graft, and the like. A bone graft may comprise up to about $10^3$, up to about $10^4$, up to about $10^5$, up to about $10^6$, up to about $10^7$, up to about $10^8$, up to about $10^9$, up to about $10^{10}$ or more cells.

The bone graft material is obtained from the donor, for example from the iliac crest, from the mandibular symphysis (chin area), from reaming, aspirating, and irrigating the femur and/or tibia, fibula, ribs, anterior mandibular ramus; parts of spinal bone, e.g. those removed during surgery, cadaver bones, etc. The graft material may be bone marrow, for example scraped from the endosteal surface of a suitable bone, or may be a block graft containing marrow and a small block of bone. Allograft bone can be taken from cadavers, bone banks, etc. for example sing a femoral head from hip replacement surgery. The bone graft material can be used fresh, or can be cryo-preserved as known in the art until it is needed.

The cells of the bone graft are suspended in a suitable culture medium in the presence of an effective dose of a liposomal Wnt protein, e.g. L-Wnt3A. Any suitable medium can be used, e.g. DMEM, RPMI, PBS, etc. Cells are typically resuspended at a concentration that maintains viability during the incubation procedure, e.g. up to about $10^4$/ml, up to about $10^5$/ml, up to about $10^6$/ml, up to about $10^7$/ml. The incubation temperature is usually not more than about 37° C., and may be lower, e.g. up to about 32° C., up to about 25° C., up to about 15° C., up to 10° C., up to about 4° C., but typically above freezing unless specifically prepared for cryopreservation.

The effective dose of the Wnt protein may vary depending on the source, purity, preparation method, etc. Where the Wnt protein is L-Wnt3A, the effective dose is usually at least about 0.1 µg/ml, at least about 0.5 µg/ml, at least about 1 µg/ml, at least about 2.5 µg/ml, at least about 5 µg/ml, at least about 7.5 µg/ml, at least about 10 µg/ml, at least about 15 µg/ml, and may be at least about 25 vg/ml, at least about 50 µg/ml, at least about 100 µg/ml.

The bone graft material is incubated with the Wnt protein for a period of time sufficient to enhance osteogenic capacity. The enhancement can be measured in various ways, e.g. by increased expression of Axin2, by increased mitotic activity in the bone graft material (measured at from about day 2 to about day 6 post-transplantation; by increased bone formation post-transplantation, by increased expression of Runx2 or Osteocalcin, by reduced apoptosis post-transplantation; or by volume of bone produced post-transplantation. The volume of increased bone may be about 1.5-fold, about 2-fold, about 3-fold or more relative to the volume that would be obtained in the absence of wnt treatment.

The bone graft material is usually contacted with the Wnt protein for at least about 1 hour, at least about 2 hours, and up to about 36 hours, up to about 24 hours, up to about 18 hours, up to about 15 hours, up to about 12 hours, up to about 8 hours, up to about 6 hours, up to about 4 hours.

Following incubation, the bone graft material may be transplanted into a recipient following conventional protocols, e.g. for repair of spinal bone, fractures, dental supports, and the like.

Osteogenic capacity is particularly restored to aged bone grafts by incubation with the a Wnt protein. Initially, liposomal Wnt3a treatment reduces cell death in aged bone grafts. Later after transplantation, bone grafts treated with liposomal Wnt3a gave rise to significantly more bone ($p<0.05$). As it will be apparent from the examples, liposomal Wnt3a treatment enhanced cell survival in the graft and re-established the bone-forming ability of grafts from aged animals.

Accordingly, the present invention provides a safe, effective, and clinically applicable regenerative medicine-based strategy for revitalizing bone grafts from aged patients, and from other patients with diminished healing potential, such as, for example, smokers, diabetics, or patients, with nutritional deficits.

All scientific and patent publications, patents and patent applications cited in this specification are herein incorporated by reference as if each individual publication were specifically and individually indicated to be incorporated by reference. Further details of the invention are provided in the following non-limiting Examples.

Example I

Wnt3a Reestablishes Osteogenic Capacity to Bone Grafts from Aged Animals

Age-related fatty degeneration of the bone marrow contributes to delayed fracture-healing and osteoporosis related fractures in the elderly. The mechanisms underlying this fatty change may relate to the level of Wnt signaling within the aged marrow cavity. In youth, long bones are filled with heme-rich marrow; with age, this is replaced by fatty marrow. Age-related fatty degeneration of the marrow is strongly associated with delayed skeletal healing and osteoporosis-related fractures in the elderly, which constitutes a growing biomedical burden. Consequently, considerable effort has gone into understanding the conversion of bone marrow into a predominantly fatty tissue. This fatty degeneration of the bone marrow occurs in parallel with a loss in osteogenic potential, which is revealed when marrow is used clinically for bone grafting purposes.

A patient's own bone and marrow is considered the "gold standard", but these autografts are oftentimes inadequate when the patient is elderly. There are at least multiple, distinct stem/progenitor cell populations that reside in the bone marrow cavity, including mesenchymal stem cells (MSCs). Although MSCs can give rise to cartilage, bone, fat, and muscle cells when cultured in vitro, MSCs residing in the marrow cavity itself only differentiate into an osteogenic or an adipogenic lineage, and growing evidence indicates that this adipogenic-osteogenic fate decision is regulated by beta catenin-dependent Wnt signaling. For example, enhancing Wnt signaling, by activating mutations in the Wnt LRP5 receptor, causes a high bone mass phenotype in humans. In vitro, this same activating mutation represses adipocyte differentiation of human mesenchymal stem cells. On the other hand, reduced Wnt signaling, for example in the osteolytic disease multiple myeloma, is associated with aggressive bone loss and a concomitant increase in marrow adiopogenesis at the expense of hematopoiesis. Together these observations support a hypothesis that Wnt signaling has a positive role in stimulating osteogenesis and inhibiting adipogenesis.

Transgenic mice were used in conjunction with a syngeneic bone graft model to follow the fates of cells involved in the engraftment. Immunohistochemistry along with quantitative assays were used to evaluate Wnt signaling and adipogenic and osteogenic gene expression in bone grafts from young and aged mice. Liposomal Wnt3a protein (L-Wnt3a) was tested for its ability to restore osteogenic potential to aged bone grafts in critical size defect models created in mice and in rabbits. Radiography, micro-CT reconstruction, histology, and histomorphometric measurements were used to quantify bone healing resulting from L-Wnt3a or control, L-PBS treatment. Gene expression profiling of bone grafts demonstrated that aging was associated with a shift away from an osteogenic profile and towards an adipogenic one. This age-related adipogenic shift was accompanied by significantly reduced Wnt expression and Wnt activity ($p<0.05$) in bone grafts from aged animals.

Transgenic mice were used in conjunction with a syngeneic bone-graft model to follow the fates of cells involved in the engraftment. Immunohistochemistry along with quantitative assays were used to evaluate Wnt signaling and adipogenic and osteogenic gene expression in bone grafts from young and aged mice. Liposomal Wnt3a protein (L-Wnt3a) was tested for its ability to restore osteogenic potential to aged bone grafts in critical-size defect models created in mice and in rabbits. Radiography, microquantitative computed tomography (micro-CT) reconstruction, histology, and histomorphometric measurements were used to quantify bone-healing resulting from L-Wnt3a or a control substance (liposomal phosphate-buffered saline solution [L-PBS]).

Expression profiling of cells in a bone graft demonstrated a shift away from an osteogenic gene profile and toward an adipogenic one with age. This age-related adipogenic shift was accompanied by a significant reduction ($p<0.05$) in Wnt signaling and a loss in osteogenic potential. In both large and small animal models, osteogenic competence was restored to aged bone grafts by a brief incubation with the stem-cell factor Wnt3a. In addition, liposomal Wnt3a significantly reduced cell death in the bone graft, resulting in significantly more osseous regenerate in comparison with controls.

Liposomal Wnt3a enhances cell survival and reestablishes the osteogenic capacity of bone grafts from aged animals in an effective, clinically applicable, regenerative medicine-based strategy for revitalizing bone grafts from aged patients.

Materials and Methods

Animals.

All procedures were approved by the Stanford Committee on Animal Research. Axin2$^{LacZ/+}$ mice have been described. Beta-actin-enhanced green fluorescent protein (ACTB-eGFP) transgenic mice (The Jackson Laboratory, Sacramento, Calif.) were chosen because of robust expression levels of GFP in bone, marrow, and other relevant cell populations. ACTB-eGFP transgenic mice were crossed with Axin2$^{LacZ/+}$ mice to obtain Axin2$^{LacZ/+}$, Axin2$^{LacZ/+}$/ACTB-eGFP, ACTB-eGFP and wild-type (WT) mice; twelve to sixteen weeks old mice were considered young; mice greater than forty weeks of age were considered aged. Aged (eight months) New Zealand white rabbits were used. One rabbit served as the bone graft donor, and nine rabbits served as experimental animals.

Bone-Grafting in Mice.

Host mice (male only) were anesthetized by intraperitoneal injection of ketamine (80 mg/kg) and xylazine (16 mg/kg). A 3-mm incision was made to expose the parietal bone; a circumferential, full-thickness defect with a 2-mm diameter was created with use of a micro dissecting trephine; the dura mater was not disturbed. Bone graft was harvested from the femora and tibiae, pooled, and divided into aliquots. Each 20-μL aliquot was incubated in 10 μL of Dulbecco modified Eagle Medium (DMEM) with 10% fetal bovine serum (FBS) containing liposomal phosphate-buffered saline solution (L-PBS) or liposomal Wnt3a protein (L-Wnt3a) (effective concentration=0.15 μg/mL) at 37° C. while the calvarial defect was prepared. Bone grafts were transplanted to the calvarial defect, and the skin was closed.

Bone-Grafting in Rabbits.

Host rabbits were anesthetized with a subcutaneous injection of glycopyrrolate (0.02 mg/kg) and buprenorphine (0.05 mg/kg), an intramuscular injection of ketamine (35 mg/kg) and xylazine (5 mg/kg), and an intravenous injection of cefazolin (20 mg/kg), and maintained under 1% to 3% isoflurane. A 2.5-cm incision was made, the ulnar border was visualized, and a 1.5-cm segmental defect was created with an oscillating saw (Stryker System 5, Kalamazoo, Mich.). The segment was removed along with its periosteal tissues. Bone graft was harvested from the pelvis and femur, pooled, and divided into aliquots. Each approximately 400-mg aliquot was combined with L-PBS (500 μL) or L-Wnt3a (effective concentration=0.5 μg/mL) and kept on ice on the back table while the ulnar defect was created in host rabbits. Bone grafts were transplanted to the ulnar defect, and the muscle and skin were closed. The procedure was performed bilaterally (i.e., both sides either received L-PBS or L-Wnt3a). This approach eliminated the possibility, however remote, that the bone graft would have an unanticipated systemic effect.

In Vitro Wnt Stimulation of Rabbit Bone Marrow.

Bone marrow from aged rabbits was incubated with L-PBS or L-Wnt3a (effective concentration=0.15 μg/mL) at 37° C. for twelve hours. Total DNA was assayed with use of PicoGreen dsDNA kit (Life Technologies, Carlsbad, Calif.) to ensure that grafts had equivalent cell volumes. Caspase activity was assayed with use of a standard kit (Roche Diagnostics, Indianapolis, Ind.).

Tissue Preparation.

Immediately after euthanasia (time points specified in each experiment), the entire skeletal element, including muscle, connective tissue, and/or dura was harvested, removed of its epidermis, and fixed in 4% paraformaldehyde at 4° C. for twelve hours. Samples were decalcified in 19% EDTA (ethylenediaminetetraacetic acid) before embedding in paraffin, or in optimal cutting temperature (OCT) compound. Sections were 10-μm thick.

Histology, Immunohistochemistry, and Histomorphometric Analyses.

Immunohistochemistry was performed as previously described. Antibodies used included rabbit polyclonal anti-green fluorescent protein (anti-GFP) (Cell Signaling Technology, Danvers, Mass.), rabbit polyclonal anti-DLK1 (EMD Millipore, Billerica, Mass.), anti-peroxisome proliferator activated receptor-g (anti-PPAR-g) (Millipore), and anti-Ki67 (ThermoFisher Scientific, Waltham, Mass.). The bromodeoxyuridine (BrdU) (Invitrogen, Camarillo, Calif.) and terminal deoxynucleotidyl transferase dUTP nick end labeling (TUNEL) (Roche Diagnostics) assays were performed following the manufacturers' instructions.

Movat pentachrome, aniline blue, Xgal, and alkaline phosphatase (ALP) stainings were performed as previously described. Tissue sections were photographed with use of a Leica DM5000B digital imaging system (Leica Microsystems, Wetzlar, Germany). A minimum of five tissue sections per sample was used for histomorphometric analyses.

Microquantitative Computed Tomography (Micro-CT) Analyses.

Mice were anesthetized with 2% isoflurane and scanned with use of a multimodal positron emission tomography-computed tomography data-acquisition system (Inveon PET-CT; Siemens, Erlangen, Germany) at 40-mm resolution. Data were analyzed with MicroView software (GE Healthcare, Chicago, Ill.). The three-dimensional region-of-interest tool was used to assign the structure and bone volume for each sample.

Assessment of the regenerate bone volume fraction (the percentage calculated by dividing the total bone volume by the regenerate bone volume [BV/TV, %]) was performed with use of high-resolution micro-CT (vivaCT 40; Scanco Medical, Brüttisellen, Switzerland) and with 70 kVp, 55 μA, 200-ms integration time, and a 10.5-μm isotropic voxel size. The region of interest was 2 cm in length and began 250 μm proximal to the edge of the defect and extended 250 μm distally beyond the opposing edge of the defect (1.5 cm total diameter). Bone was segmented from soft tissue with use of a threshold of 275 mg/cm$^3$ hydroxyapatite. Scanning and analyses adhered to published guidelines.

Quantitative Reverse Transcription-Polymerase Chain Reaction (qRT-PCR).

Tissue samples were homogenized in TRIzol solution (Life Technologies). RNA was isolated (RNeasy; Qiagen, Germantown, Md.) and reverse transcription was performed (SuperScript III Platinum Two-Step qRT-PCR Kit, Life Technologies) as described previously.

Statistical Analyses.

Results are presented as the mean plus the standard deviation, with "n" signifying the number of samples analyzed. Significant differences between data sets were determined with use of two-tailed Student t tests and nonparametric Wilcoxon tests. Significance was attained at $p<0.05$, and all statistical analyses were performed with GraphPad Prism software (GraphPad Software, San Diego, Calif.).

Results

Bone-Marrow Grafts have Osteogenic Potential.

To follow the fate of the bone-graft material, we harvested whole bone marrow from ACTB-eGFP transgenic mice, subdivided it into equivalent-size aliquots (FIG. 1-A), then transplanted it into a nonhealing, critical-size skeletal defect that was created in the calvarium of syngeneic host mice (FIG. 1-B). The viable grafted cells and their progeny were identifiable within the injury site by their GFP label (FIG.

1-C). When the donor and host were not genetically identical, most of the grafted cells died; for that reason, only syngeneic, immunologically compatible donor-host combinations were used.

On post-graft day 1, GFP-positive cells, along with stromal tissue from the GFP-positive donor, occupied the injury site (FIG. 1-C). On day 5, BrdU staining confirmed the robust proliferation of cells in the defect site (FIG. 1-D). On day 7, GFP immunostaining confirmed that grafted cells, or their progeny, remained at the defect site (FIGS. 1-E and 1-F). The grafted cells and/or their progeny eventually differentiate into osteoblasts and heal the defect (FIGS. 1-H and 1-J); in the absence of a bone graft, the defect will not heal (FIGS. 1-G and 1-I).

Aged Bone Grafts Exhibit Fatty Degeneration.

With aging, human bone marrow undergoes fatty degeneration and a loss in osteogenic potential. A comparable age-related change is observed in mice, in which the gross appearance of murine bone marrow changes from a heme-rich, fat-free tissue in young animals to a fatty marrow in aged animals. Quantitative RT-PCR analyses of the heterogeneous cell population that constitutes a bone graft showed that relative to samples from young animals, samples from aged animals showed significantly higher expression of the adipogenic genes fatty acid-binding protein 4 (Fabp4) ($p<0.01$) and peroxisome proliferator-activated receptor gamma (PPAR-$\square$) ($p<0.01$). Simultaneous with this adipogenic shift, bone grafts from aged mice also showed significantly reduced expression levels of the osteogenic genes ALP ($p<0.05$), osteocalcin ($p<0.01$), and osterix ($p<0.05$). Thus, fatty degeneration of the bone marrow observed in humans is recapitulated in mice at both a gross morphologic level and at a quantifiable, molecular level.

Fatty Degeneration is Associated with Reduced Osteogenic Potential in a Bone Graft.

Compared with the osteogenic capacity of grafts from young animals, grafts from aged animals generated significantly less new bone (FIGS. 2-A and 2-B; quantified in 2-C; $p<0.05$). This age-related reduction in osteogenic potential was not directly attributable to differences in engraftment efficiency. Using GFP immunostaining to identify the grafted cells, the distribution and number of GFP-positive cells was nearly equivalent between bone grafts from young and aged mice (FIGS. 2-D and 2-E; quantified in 2-F). Nor was the age-related alteration in osteogenic potential attributable to differences in the expansion of the graft: Using both BrdUincorporation (FIGS. 2-G and 2-H) and qRT-PCR for proliferating cell nuclear antigen (PCNA) (FIG. 2-I) we found nearly equivalent levels of cell proliferation in bone grafts from young and aged animals.

Figures 3A, 3B:
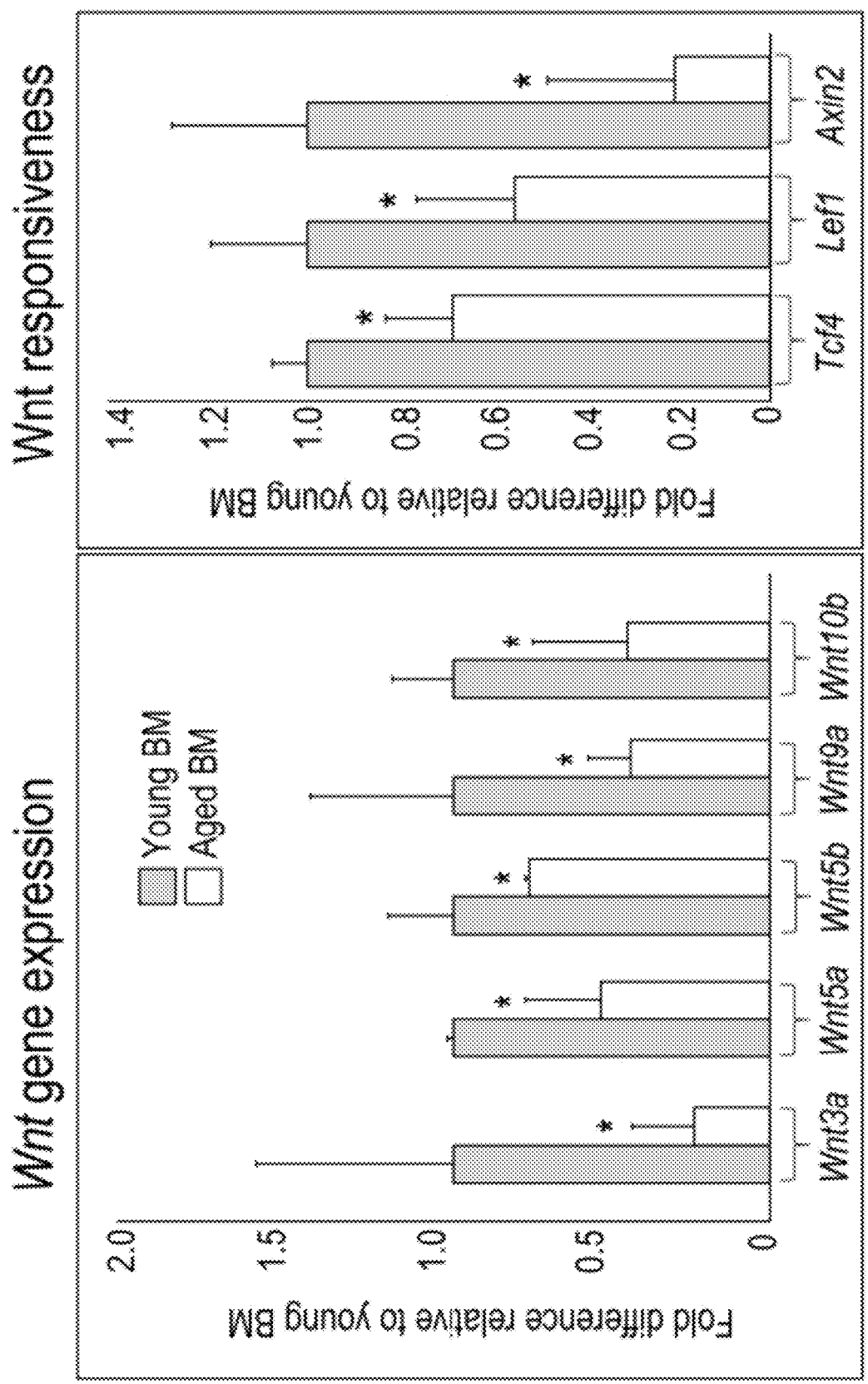
FIG. 3A-3B. Wnt signaling is reduced in aged bone grafts.
Figure 4C:
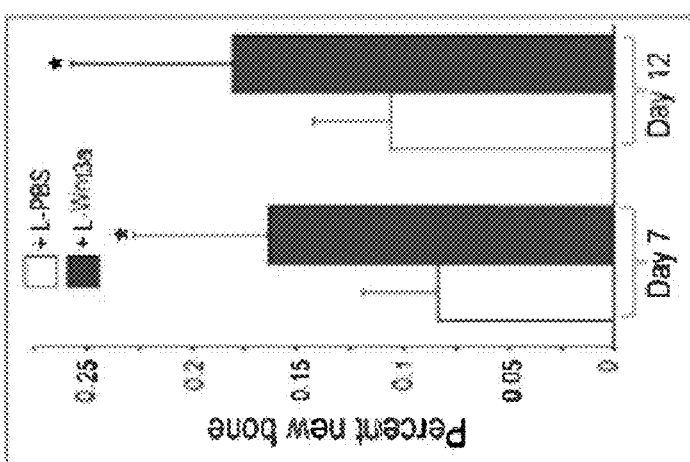
FIG. 4A-4K. Liposomal Wnt3a restores osteogenic capacity to aged bone grafts.
Figures 4A, 4B:
Figures 4D, 4E:
Figures 4F, 4G, 4H, 4I, 4J, 4K:
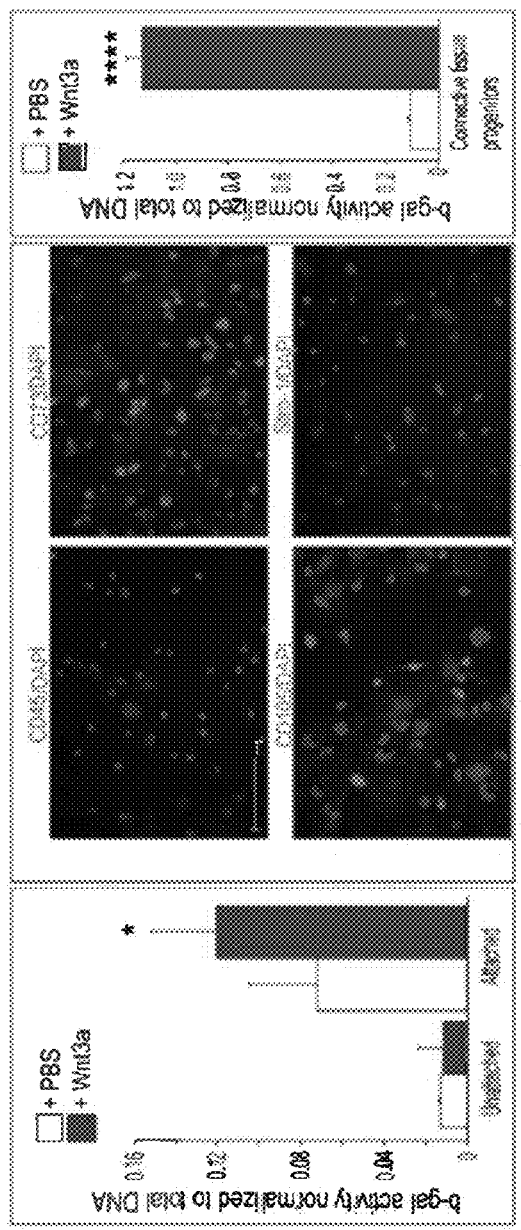

We gained insights into the basis for fatty degeneration and loss in osteogenic potential of aged bone grafts when we assessed the expression level of nineteen mammalian Wnt genes in marrow cells. A subset of Wnt genes were weakly expressed in bone marrow from aged animals compared with young animals ($p<0.05$; FIG. 3-A). This reduction in Wnt gene expression was paralleled by a reduction in Wnt responsiveness, as measured by significantly decreased expression of the Wnt direct target genes Tcf4, Lef1, and Axin2 ($p<0.05$; FIG. 3-B). These results demonstrate that Wnt signaling is reduced in aged bone marrow.

L-Wnt3a Restores Osteogenic Capacity to Bone Grafts from Aged Mice.

The first Wnt protein to be purified was Wnt3a. Wnt3a acts via the "canonical" or beta-catenin dependent pathway and is a well-known osteogenic stimulus. Given the reduced Wnt signaling in aged bone marrow, we wondered if the addition of exogenous Wnt protein would be sufficient to reestablish the osteogenic potential of bone grafts derived from aged animals.

All vertebrate Wnt proteins are hydrophobic; without a carrier, the hydrophobic Wnt3a rapidly denatures and becomes inactive. We solved this in vivo delivery problem by packaging the hydrophobic Wnt3a in lipid particles. This formulation of the human Wnt3a protein, liposomal Wnt3a (L-Wnt3a), is stable in vivo and promotes robust bone regeneration in a modified fracture model. Although exogenously applied Wnt3a has great potential as a therapeutic protein, safety remains a primary concern. The delivery of high concentrations of potent growth factors to a skeletal injury site carries with it potential oncological risk to the patient. To circumvent issues associated with prolonged or uncontrolled exposure to a growth factor, we delivered L-Wnt3a ex vivo. This was accomplished by incubating the aged bone graft with L-Wnt3a (n=30) immediately after harvest, while the recipient site was prepared. Control bone grafts were exposed to L-PBS (n=30) for the same duration.

Compared with aged grafts treated with L-PBS (FIG. 4-A), aged grafts treated with L-Wnt3a showed a dramatic enhancement in new bone formation (FIG. 4-B). Within seven days, defect sites that received L-Wnt3a-treated grafts had twofold more new bone than sites that received L-PBS treated grafts (FIG. 4-C). By day 12, L-Wnt3a-treated grafts had 1.5-fold more new bone compared with L-PBS treated grafts (FIGS. 4-D and 4-E; quantified in 4-C).

Bone-Marrow-Derived Stem Cells are Wnt Responsive.

To gain insights into which cell population(s) in the bone graft responded to the Wnt stimulus, we assayed different fractions of the marrow for Wnt responsiveness. In whole bone marrow, Wnt responsiveness was below detectable levels. We separated whole bone marrow into a non-adherent population; once again Wnt responsiveness was below the limit of detection (FIG. 4-F). In the adherent population, however, which contains connective tissue progenitor cells 53, 54, Wnt responsiveness was detected (FIG. 4-F). We then used established protocols to further enrich for bone-marrow stem and/or stromal cells from the attached population. Using immunostaining for CD45(−), CD73(+), CD105(+), and Stro1(+), we confirmed that this population was enriched for marrow-derived stem cells (FIG. 4-G). Relative to PBS-treated CD45(−), CD73(+), CD105(+), and Stro1(+) cells, the Wnt3a-treated population showed a tenfold increase in Wnt responsiveness (FIG. 4-H).

We also monitored Wnt responsiveness in bone grafts using Xgal staining of marrow from Axin2$^{LacZ/+}$ mice. Very few Xgal$^{+ve}$ cells were found in aged bone grafts (FIG. 4-I) but Xgal$^{+ve}$ cells were plentiful in young bone grafts (FIG. 4-K). Aged bone grafts were capable of responding to an L-Wnt3a stimulus, as shown by the increase in Xgal$^{+ve}$ cells following exposure (FIG. 4-J). Because the prevalence of stem cells in the murine marrow cavity is quite low, it is likely that the Wnt responsive population included more cells than the CD45(−), CD73(+), CD105(+), and Stro1(+) population.

L-Wnt3a Prevents Apoptosis in Bone Grafts.

The robust bone-inducing capacity of L-Wnt3a prompted us to extend our studies into a large animal, long-bone model. As in humans, aged rabbits experience fatty degeneration of their marrow. We utilized a critical-size ulnar defect model and transplanted aged bone grafts that had been incubated with L-PBS or L-Wnt3a into the defect. We first noted that when bone graft is harvested there is extensive programmed cell death throughout the aggregate (FIG. 5-A). The addition of L-Wnt3a significantly reduced this graft apoptosis (p<0.05) (FIG. 5-B). We verified this prosurvival effect of L-Wnt3a, using caspase activity as a measure of cell apoptosis. L-Wnt3a significantly reduced caspase activity in cells of the bone graft (p<0.05; FIG. 5-C).

L-Wnt3a Potentiates the Osteogenic Capacity of Aged Bone Grafts. L-Wnt3a and L-PBS-treated rabbit bone grafts were introduced into the critical size defect and regeneration was assessed at multiple time points. Radiographic assessment at four weeks revealed the presence of a bridging callus in sites that had received L-Wnt3a-treated graft (FIG. 5-E); in comparison, sites that received L-PBS-treated bone graft showed minimal callus formation (FIGS. 5-D).

At eight weeks, micro-CT analyses demonstrated a persistent gap in sites that were treated with L-PBS bone grafts (FIG. 5-F) whereas sites treated with L-Wnt3a bone graft exhibited robust bone formation (FIG. 5-G). Histomorphometric analyses confirmed a significant difference between the two groups, both in bone volume and in bone volume divided by total volume (FIG. 5-H).

Figures 6A, 6B, 6C, 6D, 6E, 6F:
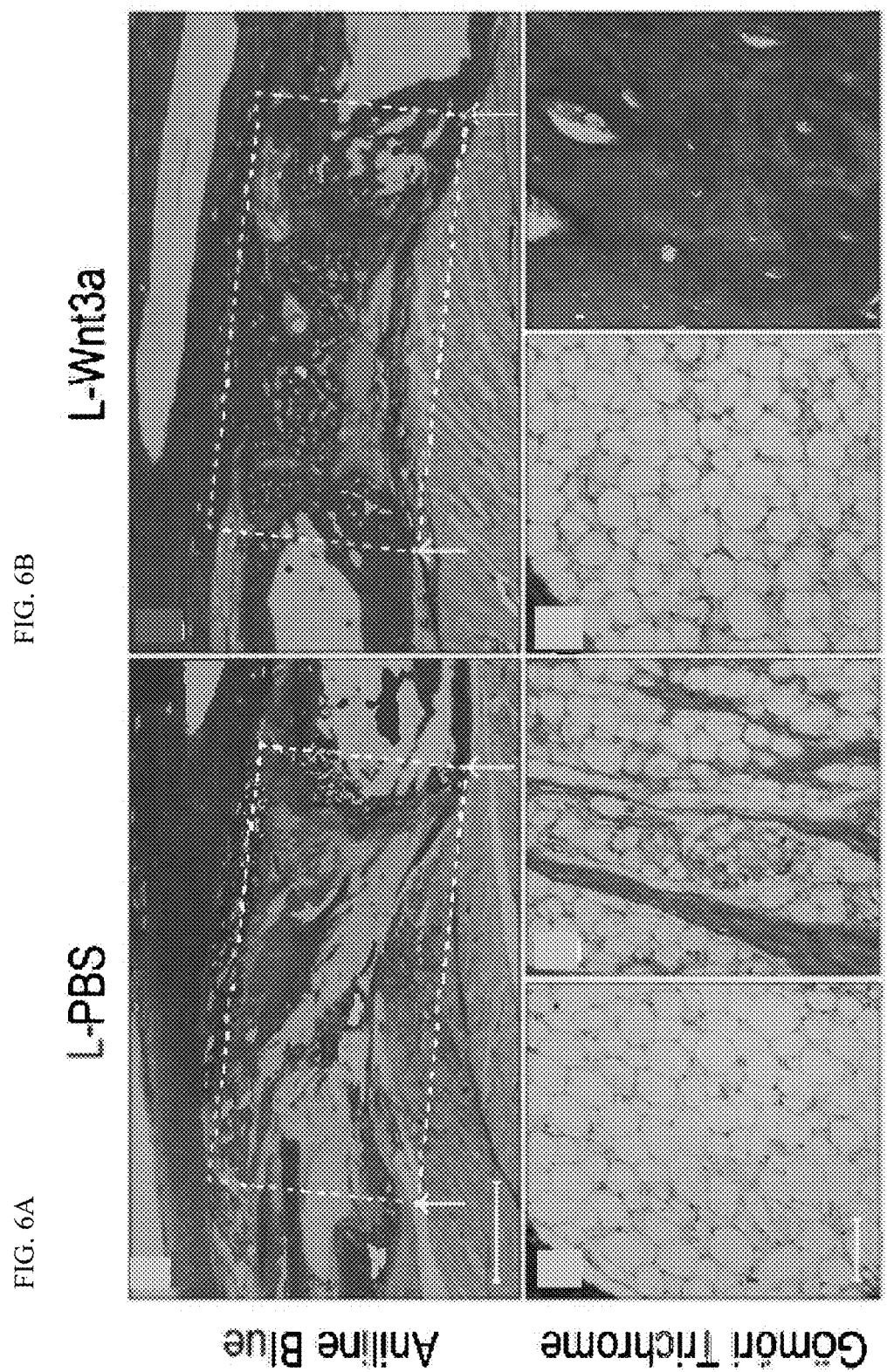
FIG. 6A-6H. Histological appearance of regenerated bone derived from L-Wnt3a treated aged bone grafts. Aniline blue staining of injury site (boxed area) treated with aged bone marrow incubated in L-PBS (FIG. 6A) or L-Wnt3a (FIG. 6B).
Figures 6G, 6H:
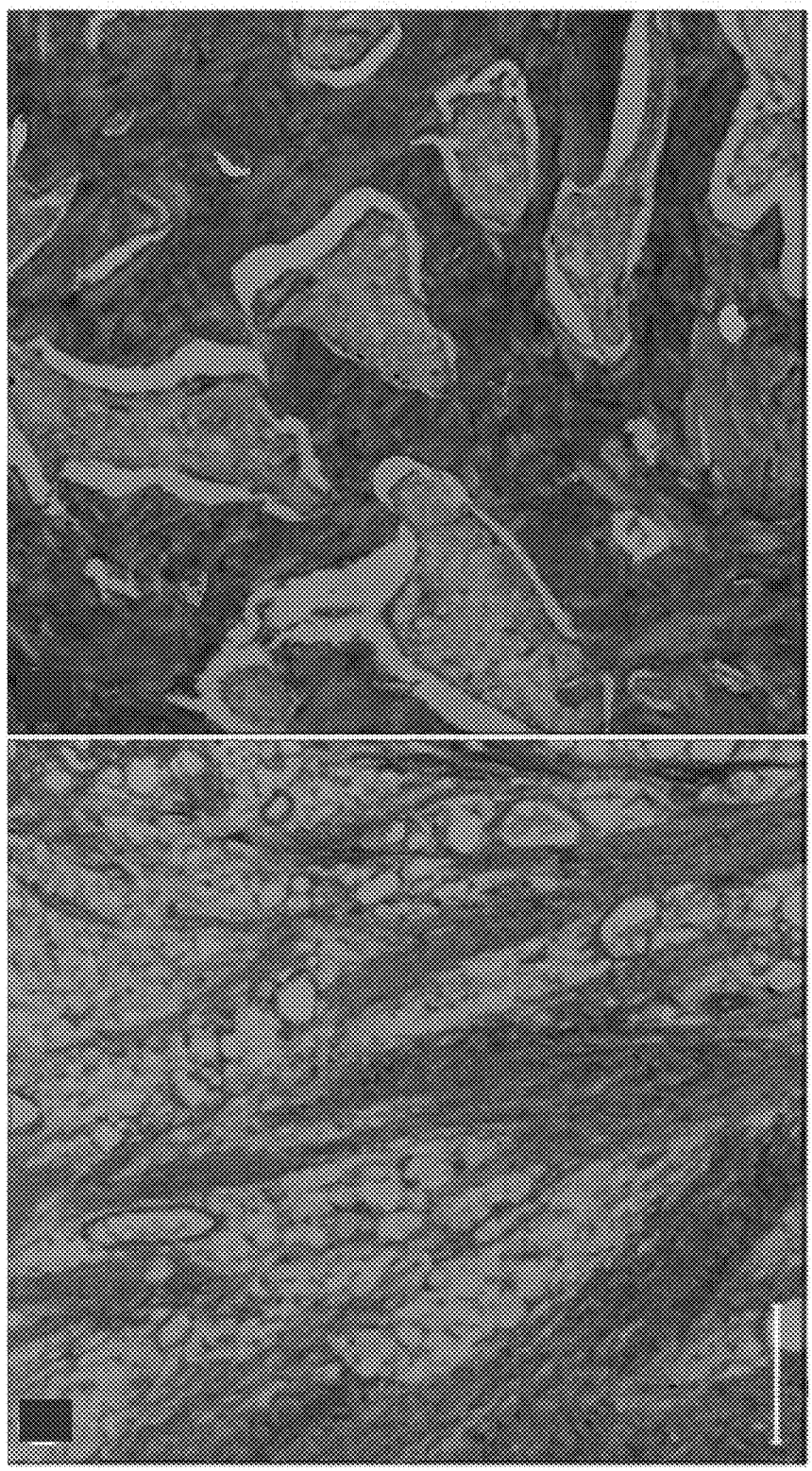

We assessed the quality of the bone regenerate. Compared with controls (FIG. 6-A), L-Wnt3a-treated injury sites were filled with new bone (FIG. 6-B). The bone marrow of the host rabbits had undergone fatty degeneration (FIG. 6-C), and a similar appearance was noted in the L-PBS-treated regenerate (FIG. 6-D). In the L-Wnt3a treated samples (FIG. 6-E), the host bone marrow showed a similar level of fatty degeneration as seen in the control animals, but the regenerate from L-Wnt3a bone graft was woven bone (FIG. 6-F) and was distinguishable from the preexisting lamellar bone by both its location in the segmental defect site and its woven appearance. Under polarized light, picrosirius red staining distinguished the mature, osteoid tissue found in the L-Wnt3a-treated bone grafts (FIG. 6-H) from the fibrous tissue of the L-PBS treated bone grafts (FIG. 6-G).

Stem-Cell and/or Progenitor Cell Populations in Bone Grafts.

The mammalian bone-marrow cavity is a functional niche that supports multiple stem-cell and/or progenitor cell populations. Marrow-derived bone grafts, which are heterogeneous by nature, contain multiple populations, including some stem cells and/or progenitor cells. The contribution of these stem cells and/or progenitor cells to an osseous regenerate, however, remains unknown. Multiple marrow-derived stem-cell populations are Wnt-responsive and, using established protocols, we confirmed that at least the CD45(−), CD73(+), CD105(+), and Stro1(+) stem-cell and/or stromal-cell population in the bone marrow is Wnt-responsive (FIG. 4).

Wnt Signaling and Age-Related Fatty Degeneration of the Marrow.

In vitro, the abrogation of Wnt signaling causes mesenchymal stem cells to differentiate into adipocytes whereas potentiation of Wnt signaling causes mesenchymal stem cells to differentiate into osteoblasts. This has direct clinical relevance: With age, human bone marrow undergoes fatty degeneration and loses its osteogenic potential. Our data show that this loss in osteogenic potential of aged bone grafts rests, in part, on a reduced level of Wnt signaling: Compared with bone grafts from young mice, aged bone grafts show a dramatic reduction in Wnt gene expression and Wnt responsiveness (FIG. 3). Adding L-Wnt3a to aged bone marrow reestablishes its bone forming capacity (FIGS. 4, 5, and 6).

Conditions associated with decreased mobility, such as extended bed rest and osteoporosis, are also associated with fatty degeneration of the marrow. Some data suggest that fatty degeneration is reversible, at least experimentally. Clearly, understanding the basis for this degeneration—and the extent to which age-related changes in the skeleton can be reduced-will be of considerable importance in devising new treatment for bone injuries in elderly patients.

Growth-Factor-Augmented Bone Regeneration:

Safety First. Safety concerns have recently arisen surrounding the use of growth factors to augment skeletal healing. Growth factor stimuli are largely thought to induce the proliferation of cells residing in the injury site; because uncontrolled proliferation is a characteristic of oncogenic transformation, this proliferative burst must be controlled both spatially and temporally. For this reason, we designed an approach that would limit whole-body exposure to L-Wnt3a. The targeted cells are those in the bone graft itself, which is incubated with L-Wnt3a ex vivo. The activated cells-rather than the growth factor itself—are then reintroduced into a defect site. This ex vivo approach restricts the L-Wnt3a stimulus spatially (to the graft itself, and not to host tissues) and temporally (exposure to the Wnt stimulus only occurs during the incubation period). This ex vivo approach is tailored to clinical use and does not require a second procedure. Thus, packaging Wnt protein into lipoparticles constitutes a viable strategy for the treatment of skeletal injuries, especially those in individuals with diminished healing potential.

Example 2

Reengineering Autologous Bone Grafts with the Stem Cell Activator WNT3A

Autologous bone grafting is the most commonly used procedure to treat bone defects, but is considered unreliable in elderly patients. The efficacy of an autograft can be traced back to multipotent stem cells residing within the material. Aging attenuates the viability and function of these stem cells, leading to inconsistent rates of bony union. We show that age related changes in autograft efficacy are accompanied by a loss of endogenous Wnt signaling in the material. We mimicked this loss of endogenous Wnt signaling by overexpressing the Wnt inhibitor Dkk1 and found that Wnt signaling is necessary for the osteogenic differentiation of an autograft. We developed an ex vivo drug delivery system in which autografts were incubated in a stabilized formulation of WNT3A protein then introduced it in vivo. The bioengineered autograft showed significantly improved survival in the hosting site. Mitotic activity and osteogenic differentiation were significantly enhanced in WNT-activated autografts compared to autografts alone. In a spinal fusion model, aged autografts treated with L-WNT3A showed superior bone forming capacity compared to autografts alone. Thus, a brief incubation in L-WNT3A reliably improves autologous bone grafting efficacy, which has the potential to significantly improve patient care in the elderly.

The most common treatment for non-unions, delayed unions and posterior cervical spine fusions is autologous bone grafting, or autografting. Autografts are successful in the vast majority of cases but the basis for their bone forming (osteogenic) capacity is not entirely clear. Autografts are a heterogeneous collection of marrow blood products, connective tissue stroma, bony extracellular matrix, and a variety of hematopoietic, vascular, and osteogenic stem cell populations and they have variously been described as osteoinductive, osteoconductive, and osteogenic. These terms, however, only describe cellular processes; they do not provide insights into the basis for the osteogenic potential of autografts.

Autografts become unreliable in older patients, and there are likely to be multiple contributing factors for this degenerative state. Some data suggests that the osteogenic capacity of autografts is dependent upon the presence of stem or progenitor cells contained within the bone graft material, and stem cell numbers are thought to decline with age in part because of accumulated DNA damage that ultimately results in cell cycle arrest and apoptosis. Other data argue that rather than a decline in the number of stem cells, their function deteriorates with age. Aged stem cells may also be less responsive to growth factor stimuli in their environments; likewise, local or systemic levels of these growth factor stimuli may decline in the elderly. Aging also impacts the mitotic capacity of stem cells: Stem cell senescence increases with age, in part because of a reduction in telomerase activity and subsequent telomere shortening. These reductions in stem cell function constrain the normally robust regenerative responses of tissues such as the intestine, and muscle. Aging also impacts the mitotic capacity of stem cells. Similar mechanisms may be responsible for the loss in osteogenic capacity of autografts.

Here, we tested the hypotheses that the osteogenic potential of an autograft is attributable to osteogenic stem cells in the graft material; that aging impacts the Wnt responsive status of these stem/progenitor populations; and that WNT-mediated activation of the stem cells can restore bone forming potential to autografts from elderly animals.

Methods

Animal care. All procedures followed protocols approved by the Stanford Committee on Animal Research. Beta-actin-enhanced green fluorescent protein (ACTB-eGFP; The Jackson Laboratory, Sacramento, Calif.) and CD1 wild type, syngeneic mice were used. Mice<3 months old were considered young; mice>10 months were considered aged. $Axin2^{CreERT/+}$; R26RmTmG/+ mice were purchased from Jackson Labs. Aged wild type Lewis rats ("retired breeders" from Charles Rivers, Mass.), were utilized for spinal fusion surgeries according to AAUC and IUPAC guidelines (protocol 13146).

Collection and treatment of bone graft material (BGM) for rodent models. Both rats and mice were employed in this study. The use of mouse models allows for a broad spectrum of molecular analyses, however, because autografts are highly invasive for these small animals, we used rats when performing autografts (e.g., FIGS. 7 and 12), and syngeneic mice when employing advanced molecular techniques (FIGS. 8-11). In all cases, bone graft material (BGM) was harvested from femurs, tibiae and iliac crest by splitting the bones lengthwise, gently scraping the endosteal surface with a sharp instrument, and irrigating the marrow contents into a collection dish. This method mimicked the RIA technique used in humans.

To induce recombination in $Axin2^{CreERT/+}$; $R26R^{mTmG/+}$ mice (FIG. 8), animals were given 160 µg/g body weight tamoxifen via IP injection or gavage for 5 consecutive days. Tissues were harvested 7 days after the first treatment and analyzed by GFP immunostaining or fluorescence.

To ensure that BGM aliquots for transplantation into the SRC were equivalent in terms of cellular content, BGM from 3 mice (littermates) was pooled then divided into 20 µL aliquots just as in the transplant assays. DNA content was extracted with the DNeasy Tissue Kit (QIAGEN) and relative DNA concentration was measured using the Quant-iT PicoGreen dsDNA Kit (Invitrogen) and microplate fluorescence reader (BERTHOLD, Bad Wildbad, Germany). The percent variation in DNA content was <20%. To obtain $BGM^{ACT}$, freshly harvested BGM was placed into 20 µL of culture medium containing a liposomal formulation of either phosphate-buffered saline (L-PBS) or WNT3A (L-WNT3A, effective L-WNT3A concentration=0.15 µg/mL) and maintained at 23° C. for 1 hour.

Quantitative Reverse Transcription-Polymerase Chain Reaction (qRT-PCR).

Tissue samples were homogenized in TRIzol solution (Invitrogen). RNA was isolated (RNeasy; Mini Kit; QIAGEN, Md., USA) and reverse transcription was performed (SuperScript III First-Strand Synthesis Supermix for qRT-PCR, Invitrogen) as described previously. Quantitative real-time PCR was carried out using Prism 7900HT Sequence Detection System (Applied Biosystems, Foster City, Calif., USA) and Power SYBR Green PCR Master Mix (Applied Biosystems). Levels of gene expression were determined by the CT method and normalizing to their GAPDH values. All reactions were performed in triplicate, means and standard deviations were calculated. Primers sequences (5' to 3') are as follows: Axin2, [for-TCATTTTCCGAGAACCCACCGC (SEQ ID NO:3)], [rev-GCTCCAGTTTCAGTTTCTCCAGCC (SEQ ID NO:4)]; Lef1, [for-AGGAGCCCAAAAGACCTCAT (SEQ ID NO:5)], [rev-CGTGCACTCAGCTATGACAT (SEQ ID NO:6)]; GAPDH, [for-ACCCAGAAGACTGTGGATGG (SEQ ID NO:7)] [rev-GGATGCAGGGATGATGTTCT (SEQ ID NO:8)]; ALP [for-ACCTTGACTGTGGT-TACTGC (SEQ ID NO:9)], [rev-CATATAGGATGGCCGT-GAAGG (SEQ ID NO:10)]; Osterix, [for-GGA-GACCTTGCTCGTAGATTTC (SEQ ID NO:11)], [rev-GGGATCTTAGTGACTGCCTAAC (SEQ ID NO:12)]; Osteocalcin, [for-TGTGACGAGCTATCAAACCAG (SEQ ID NO:13)], [rev-GAGGATCAAGTTCTGGAGAGC (SEQ ID NO:14)].

Western Analyses.

BGM was harvested from young (N=5) and aged (N=5) mice and then placed in Dulbecco's Modified Eagle Medium (DMEM) containing 10% Fetal Bovine Serum (FBS), 100 U/mL penicillin and 100 µg/mL streptomycin, and incubated at 37° C. in 5% CO2. After 24 hours, non-adherent cells were removed, media was replaced, and adherent cells were passaged until they reached confluence. Media was changed every 3 days. In some experiments, cells after passage 3 were treated with either L-PBS or L-WNT3A (effective concentration=0.03 µg/mL). In these experiments, cells were collected 24 h later and lysed using RIPA buffer (Sigma-Aldrich, St. Louis, Mo., USA). Total protein was extracted for Western analysis. Pan-actin was used as an internal control and to ensure protein integrity. Antibodies against WNT3A (R&D, Minneapolis, Minn., USA), non-phosphorylated β-catenin (Cell Signaling, Danvers, Mass., USA), and Axin2 (Abcam, Cambridge, Mass., USA) were used. Integrated intensity was analyzed by ImageJ (National institute of Health, USA version 1.47v) to quantify Western blotting results.

Sub-Renal Capsule Transplant Surgery.

In some cases, the sub-renal capsular assay (SRCA) was employed to assay its differentiation potential. Following inhalation of anesthesia by the syngeneic host mice, a skin incision was made on the left flank directly caudal to the rib cage. The peritoneal cavity was opened to expose the kidney. A small incision was created in the renal capsule and the BGMs were carefully placed under the capsule using soft plastic tubing. The kidney was then returned to the peritoneal cavity, and the peritoneum and skin were closed with sutures. Buprenorphine (0.05 mg/kg) was used for analgesia. In cases where the BGM was harvested from $Axin2^{CreERT2}$; $R26^{mTmG}$ donors, hosts were subsequently provided tamoxifen by gavage (100 µL of 10 mg/mL) beginning on day 0 for 5 days. The SRC transplants were harvested at the time points indicated. 2.6 Adenovirus-mediated inhibition of Wnt signaling DKK1 and the negative control Fc adenoviral constructs were described previously. The adenoviral constructs were transfected into 293T cells. After 2 days, cells were collected, lysed, and precipitated by centrifugation. The purified adenovirus was aliquoted and stored at −80° C. Wnt inhibition was achieved by in vitro incubation of BGMs with Ad-Dkk1 and the control Ad-Fc for 2 hours, and the BGM aliquots were then transplanted into calvarial defects.

Calvarial Critical-Size Defect Surgery.

Mice were anesthetized, and a 3-mm incision was made to expose the parietal bone. A circumferential, full-thickness defect with a 2-mm diameter was created with the use of a micro-dissecting trephine; the dura mater was not disturbed. BGM aliquots were incubated with Ad-Dkk1 and the control Ad-Fc for 2 hours. BGM aliquots were then transplanted into the calvarial defect and the skin was closed with sutures Following recovery from surgery, mice received Buprenorphine for analgesia. Micro-computed tomography (Micro-CT) analyses were performed as previously described.

Spinal Fusion Surgery.

Lewis Rats were anesthetized using a cocktail of Ketamine 70-100 mg/kg and Xylazine 5-10 mg/kg. The lumbar region of the rats were shaved then disinfected with Betadinesoaked gauze. Prior to the skin incision, the rats were injected with the analgesia buprenorphine 0.02 mg/kg SC/IP. First, bone graft material (BGM) was harvested from the iliac crest; briefly, the left iliac spine was palpated and a vertical cutaneous incision was made; the dorsal crest of the iliac spine was accessed and exposed through blunt dissection. The attached muscle and periosteum were elevated and 0.3 g of BGM was harvested with a rongeur forceps and morselized. BGM was then incubated with either with 100 µL L-PBS or with 100 µL of [0.15 µg/mL] L-WNT3A while the transverse processes were exposed. To expose the transverse processes, posterolateral blunt dissection was carried down and the reflected paraspinal muscles were held in place by retractors. The transverse processes of L4-L5 were cleaned of periosteum and decorticated with a high-speed burr. The BGM was spread over and between the L4-L5 transverse processes. The paraspinal muscles were closed with absorbable sutures (4-0 Vicryl) and the skin with interrupted nonabsorbable sutures (4-0 Nylon). The surgical site was treated with an antibiotic ointment. 10 mg/kg Baytril was delivered subcutaneously. Buprenorphine (0.02 mg/kg) was administered after surgery for 3 days, and subsequent doses were given as needed to control pain.

Sample Preparation, Tissue Processing, Histology.

Tissues were fixed in 4% paraformaldehyde (PFA) overnight at 4° C. Samples were decalcified in 19% EDTA for 1 day. Specimens were dehydrated through an ascending ethanol series prior to paraffin embedding. Eight-micron-thick longitudinal sections were cut and collected on Superfrost-plus slides for histology. Safranin O, Aniline blue and Gomori staining were performed as previously described. Tissue sections were photographed using a Leica DM5000B digital imaging system (Leica Micro-systems, Wetzlar, Germany).

ALP, TRAP and TUNEL Staining.

Alkaline phosphatase (ALP) activity was detected by incubation in nitro blue tetrazolium chloride (NBT; Roche, Indianapolis, Ind., USA), 5-bromo-4-chloro-3-indolyl phosphate (BCIP; Roche), and NTM buffer (100 mM NaCl, 100 mM Tris pH 9.5, 5 mM MgCl). Tartrate-resistant acid phosphatase (TRAP) activity was observed using a Leukocyte acid phosphatase staining kit (Sigma, St. Louis, Mo., USA) following manufacturer's instructions. After developing, slides were dehydrated in a series of ethanol, cleaned in Citrisolv (Fisher Scientific), and cover-slipped with Permount mounting media (Fisher Scientific). For TUNEL staining, sections were permeabilized using 0.1% Triton X-100 (Sigma) and 0.1% sodium citrate (sigma), and incubated with TUNEL reaction mixture (In Situ Cell Death Detection Kit, Roche). Sections were mounted with DAPI mounting medium (Vector Labs, Burlingame, Calif., USA) and visualized under an epifluorescence microscope. For bromodeoxyuridine (BrdU) assay, mice were given intraperitoneal injections of BrdU labeling reagent (Invitrogen, Calif., USA) and euthanized 4 hours post-injection. BrdU detection was carried out using BrdU Staining Kit (Invitrogen, CA, USA) following the manufacturer's instructions.

Immunohistochemistry.

Tissue sections were deparaffinized and rehydrated in PBS. Endogenous peroxidase activity was quenched by 3% hydrogen peroxide for 5 min, and then washed in PBS. Slides were blocked with 5% goat serum (Vector laboratories) for 1 hour at room temperature. The appropriate primary antibody was added and incubated overnight at 4° C. Samples were then incubated with appropriate biotinylated secondary antibodies (Vector Laboratories) and advidin/biotinylated enzyme complex (Vector Laboratories) and developed by a DAB substrate kit (Vector Laboratories). Antibodies used include GFP (cell signaling) and DLK1 (Millipore), Runx2 (Santa Cruz), Sox9 (Abcam) and PPAR-γ (Cell Signaling).

Micro-CT Analyses and Quantification of Graft Growth.

Scanning and analyses adhered to published guidelines]. Mice were anesthetized with 2% isoflurane and scanned with use of a multimodal positron emission tomography computed tomography data-acquisition system (Inveon PET-CT; Siemens, Erlangen, Germany) at 40-mm resolution. To define the graft growth that occurred in each sample, POD2 and POD49 timepoint scanning data were exported into Osirix software version 5.8 (Pixmeo, Bernex, Switzerland) and registered for segmentation in the same orientation. The new that bone formed was compared to the initial BGM volume transplanted. Differences between sets of data were determined by using Mann-Whitney test in XLStat software version (Addinsoft, Paris, France). A p-value<0.05 was considered statistically significant.

Quantification and Statistical Analyses.

GFP, BrdU, TUNEL, DLK1, Osteocalcin and Aniline blue stainings were quantified. Photoshop CS5 (Adobe, version 10.0.1) was used to determine the number of pixels in the region of interest (ROI), at the injury site. The magic wand tool was used to assign the area of positive pixels within the ROI. The ratio of pixels of positive signals to pixels of ROI was expressed as a percentage. At least 5 sections evenly spaced across the injury sites were quantified to determine the average value of each sample. Five samples were included in each group (n=5). Results are presented as the mean±SD. Student's t-test was used to quantify differences described in this article. P<0.05 was considered significant.

Results

Bone Graft Material Contains Multiple Stem/Progenitor Cell Populations.

Figures 7A, 7B, 7C:
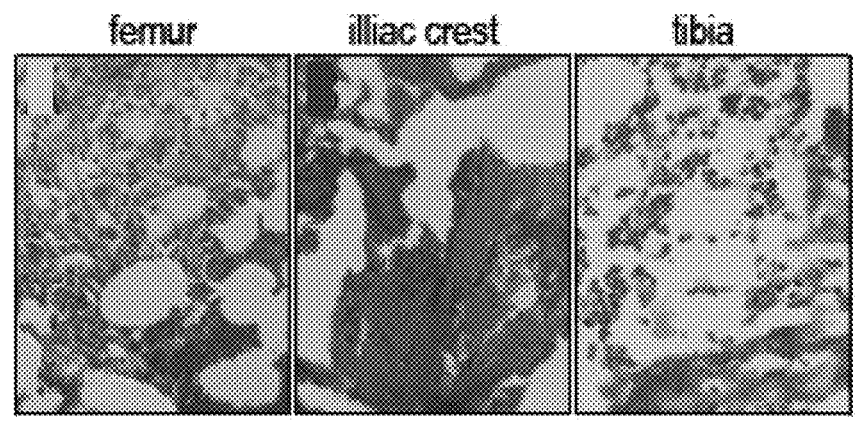
Figure 7D:
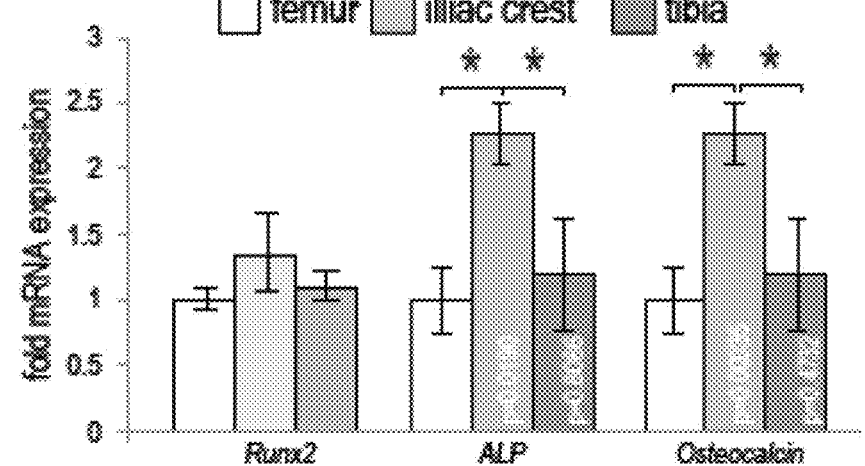
Figure 7E:
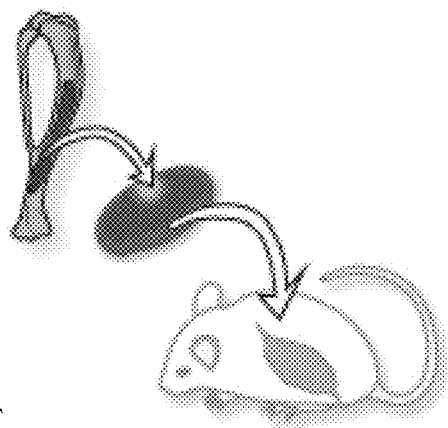
Figure 7F:
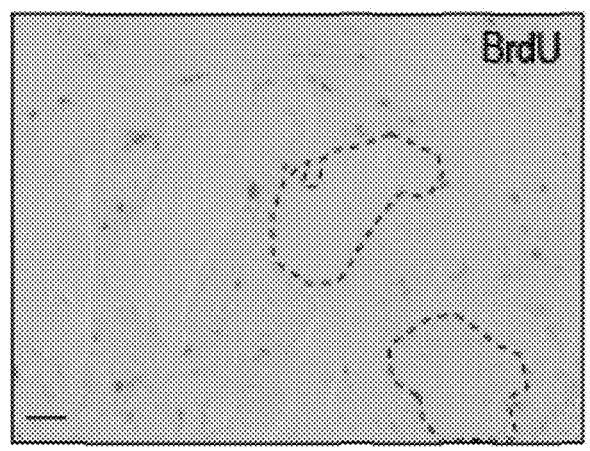

The optimal anatomical site for harvesting autografts depends upon a number of factors including donor site morbidity and the availability of bone stock. We harvested BGM from three anatomical sites using a modified reamer-irrigator-aspirator (RIA) technique and noted that the femur, iliac crest, and tibia yielded BGM with distinctly different histological appearances. In addition to hematopoietic cells, femur BGM contained adipocytes, even when harvested from young animals (FIG. 7A). Iliac crest BGM was largely comprised of trabecular bone fragments covered in tightly adherent cells (FIG. 7B). BGM from the tibia contained a considerable amount of fibrous stroma and small, anucleated cells (FIG. 7C). We used quantitative RT-PCR to evaluate endogenous osteogenic gene expression and found that of the three sources, iliac crest BGM expressed alkaline phosphatase and Osteocalcin at significantly higher levels (FIG. 7D). In general, it is widely believed that the osteogenic property of an autograft is attributable to stem/progenitor cell populations and osteoblasts within the bone graft material (BGM). We directly tested this hypothesis by transplanting BGM into a sub-renal capsule (SRC) assay. The SRC provides a vascular supply to the transplanted tissue and supports the differentiation of cells into multiple kinds of tissues including bone, skin, muscle, teeth, organs, and tumors. BGM was harvested from the iliac crest then transplanted beneath the animal's kidney capsule (FIG. 7A) and allowed to develop there for 7 days. BrdU incorporation demonstrated the high mitotic activity of cells in the autologous BGM (FIG. 7B). Immunostaining for Runx2 (FIG. 7C), Sox9 (FIG. 7D) and PPARγ (FIG. 7E) demonstrated that subsets of cells in the BGM expressed gene markers associated with osteogenic, chondrogenic and adipogenic commitment. On day 7, a sub-population of BGM-derived cells had differentiated into bone (FIG. 7F), cartilage (FIG. 7G), and fat (FIG. 7H). Together, these data demonstrated that the BGM contains stem/progenitor cells capable of differentiating into all three lineages.

Wnt Signaling in Bone Graft Material Declines with Age.

Wnts are among the best studied of the molecular signals that induce osteogenic differentiation. Using $Axin2^{CreERT2}$; R26 $m^{TmG}$ reporter mice we induced recombination (see Methods) then identified $GFP^{+ve}$ pre-osteoblasts in the periosteum (FIG. 8A) and the endosteum (FIG. 8B). The frequency of $GFP^{+ve}$ cells in the endosteum was ~0.1% (FIG. 8C). $GFP^{+ve}$ cells were also identified in freshly harvested BGM (FIG. 8D). Thus, a subset of cells in the heterogeneous BGM is Wnt responsive. We compared the Wnt responsive status of BGM from young (<3 month old) and aged (>10 month old) mice. Quantitative absolute RT-PCR demonstrated that expression of the Wnt target genes Axin2 and Lef1 was almost two-fold lower in BGM harvested from aged mice ($BGM^{aged}$) v. young mice ($BGM^{young}$; FIG. 8F). Western analysis confirmed that Wnt3a, phosphorylated beta catenin, and Axin2 expression were all significantly lower in $BGM^{aged}$ compared to $BGM^{young}$ (FIG. 8G). Thus, the endogenous Wnt responsive status of BGM deteriorates with age.

Osteogenic Differentiation Capacity Also Declines with Age.

Figure 9I:
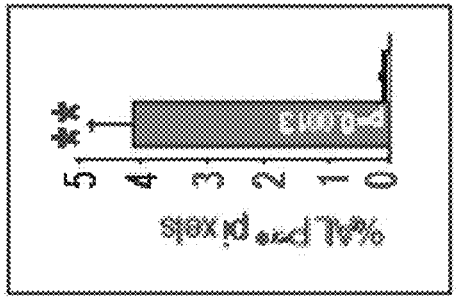
Figure 9L:
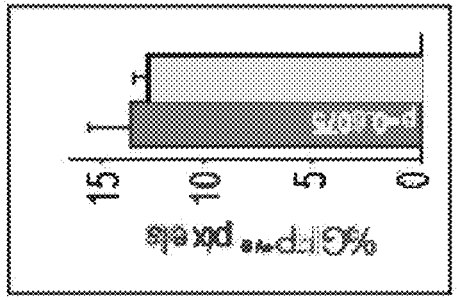

In humans, the rate of bone healing declines with age. We found a similar age-related decline in the osteogenic capacity of BGM. Freshly harvested $BGM^{aged}$ showed significantly lower expression levels of the osteogenic genes Alkaline phosphatase, Osterix, and Osteocalcin compared to freshly harvested $BGM^{young}$ (FIG. 9A). To test whether the reduction in osteogenic gene expression affected the osteogenic capacity of the BGM we returned to the SRC assay. Performing an autograft in a mouse, however, is excessively traumatic. To mimic an autograft, we used syngeneic donors and hosts. Because syngeneic animals are so closely related, their tissues are immunologically compatible and transplantation of tissues does not provoke an immune response. ACTB-eGFP mice served as the donors and BGM was readily identifiable in the SRC by its GFP fluorescence (FIG. 9B, C).

Figure 9H:
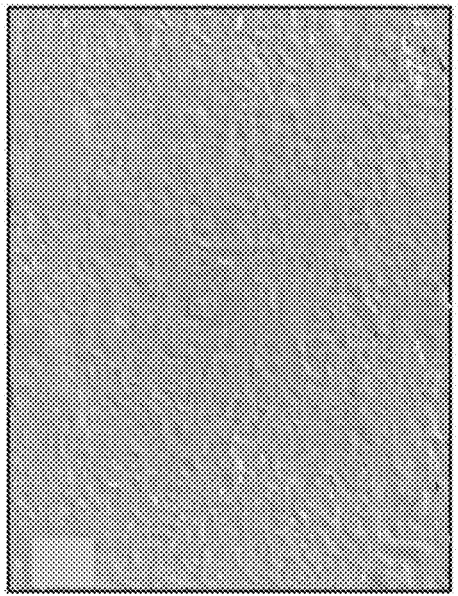
Figure 9K:
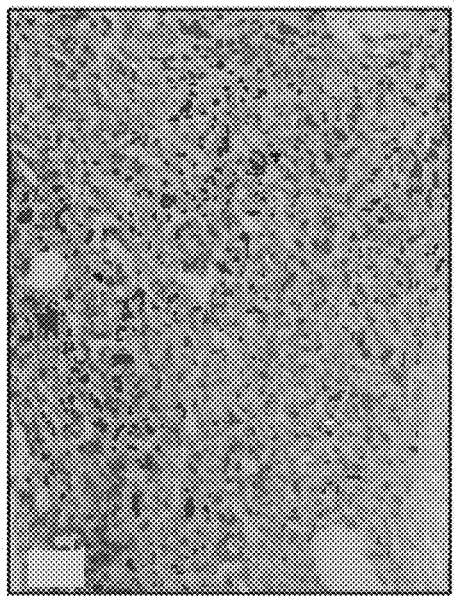
Figure 9G:
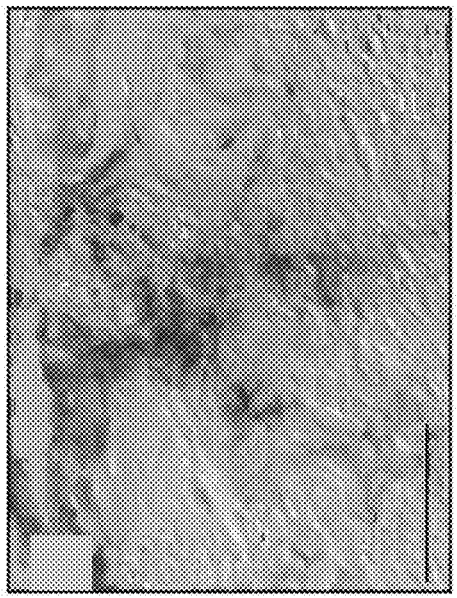
Figure 9J:
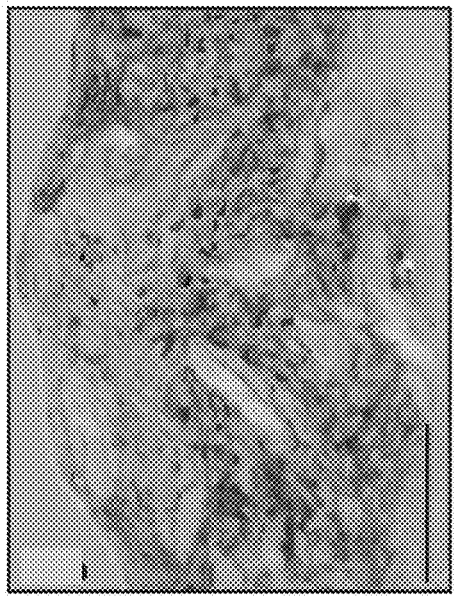

Seven days after transplantation, BGM was harvested and analyzed for evidence of bone formation. Aniline blue stained osteoid matrix was evident in $BGM^{young}$ (FIG. 9D) but absent in $BGM^{aged}$ (FIG. 9E; quantified in F). The osteoid matrix in $BGM^{young}$ was undergoing mineralization as shown by ALP staining (FIG. 9G) whereas $BGM^{aged}$ showed no ALP staining (FIG. 9H; quantified in I). We wondered if engraftment efficiency between $BGM^{aged}$ and $BGM^{young}$ could account for the differences in osteogenic differentiation but GFP immunostaining demonstrated that in both $BGM^{young}$ (FIG. 9J) and $BGM^{aged}$ (FIG. 9K) there were a similar number of surviving donor cells (quantified in FIG. 9L). Together these data indicate that osteogenic gene expression and osteogenic capacity of BGM declines with age.

Wnt Signaling is Necessary for the Osteogenic Capacity of BGM.

Endogenous Wnt responsiveness, and the osteogenic capacity of BGM, diminishes with age. To test whether reduced Wnt signaling contributed to this age-related decline in osteogenic potential, we blocked endogenous Wnt signaling in BGM. Others and we have used over-expression of the Wnt inhibitor, Dkk1 to transiently abolish Wnt signaling in vivo. We delivered either Ad-Dkk1 or Ad-Fc (control) to the bone marrow cavity of young mice then harvested $BGM^{young}$ 24 h later and transplanted the aliquots into critical size (non-healing) skeletal defects. Seven days later, when control $BGM^{young}$ was strongly positive for ALP activity (FIG. 10A), Ad-Dkk1 treated $BGM^{young}$ showed minimal activity (FIG. 10B). Instead, Ad-Dkk1 treated $BGM^{young}$ showed widespread expression of the adipogenic proteins PPAR-□□(FIG. 10C,D) and Dlk1 (FIG. 10E,F). Bone formation was repressed by Ad-Dkk1 treatment, as shown by micro-CT (FIG. 10G,H; quantified in I) and histomorphometric analyses of the BGM (FIG. 10J,K; quantified in L). Thus, the osteogenic capacity of BGM relies upon an endogenous Wnt signal.

Augmenting the Endogenous Wnt Signal in $BGM^{aged}$ Restores its Osteogenic Capacity.

Figures 11A, 11B, 11C, 11D, 11E, 11F:
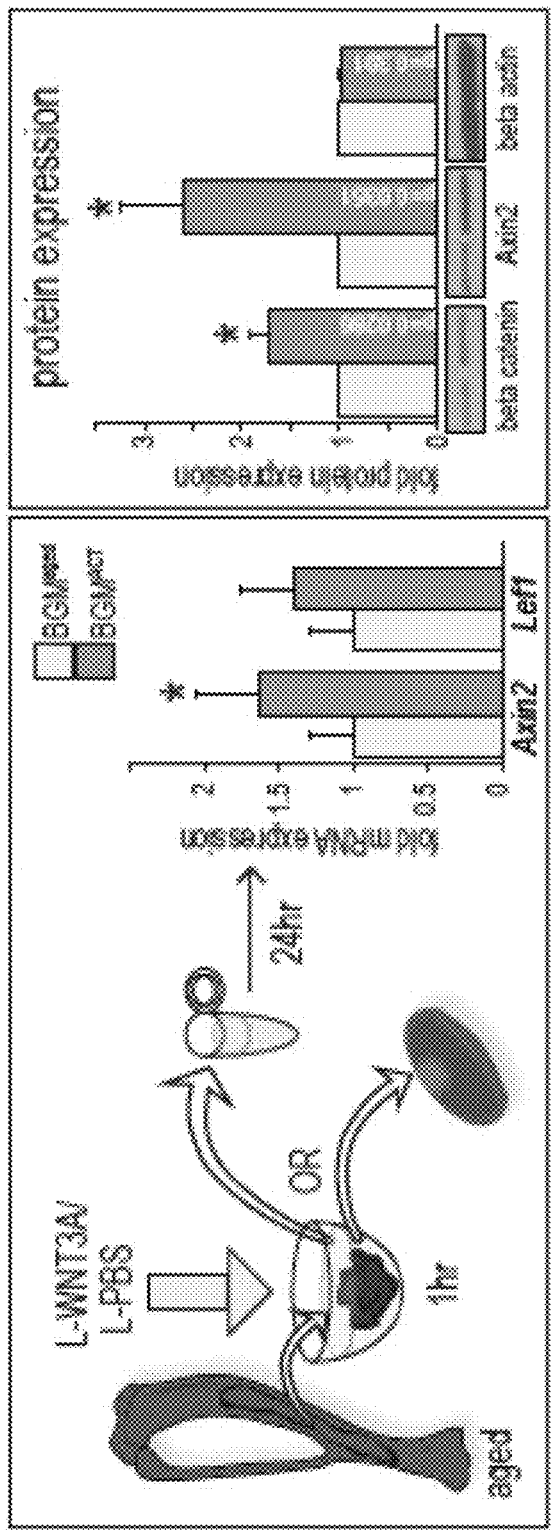

Endogenous Wnt signaling is necessary for BGM to exhibits its osteogenic capacity (FIG. 10J-L). We next tested whether a Wnt stimulus was sufficient to enhance BGM efficacy. $BGM^{aged}$ was harvested, treated with L-WNT3A or liposomal PBS (L-PBS) then incubated at 37° C. (FIG. 11A). Absolute qRT-PCR analyses revealed a small but significant elevation in Axin2 expression (FIG. 11B). Lef1 was modestly elevated in response to L-WNT3A (FIG. 11B). Western analyses indicated that both beta catenin and Axin2 proteins were elevated in response to L-WNT3A (FIG. 11C). Mitotic activity in BGM was increased by L-WNT3A treatment. On post-transplant day 4, cell proliferation was significantly increased in L-WNT3A treated $BGM^{aged}$ compared to LPBS-treated $BGM^{aged}$(FIG. 11D, E; quantified in F). The effect on cell cycling was transient: by post-transplant 7, BrdU incorporation was equivalent between the L-PBS and L-WNT3A samples (FIG. 11G,H; quantified in I). Cell differentiation in $BGM^{aged}$ was evaluated. Expression of the adipogenic protein Dlk1 was lower (FIG. 11J,K; quantified in L) and expression of the osteogenic protein Osteocalcin was higher in L-WNT3A treated $BGM^{aged}$ (FIG. 11M,N; quantified in O). New bone formation was found only in L-WNT3A treated $BGM^{aged}$ (FIG. 11P,Q; quantified in R). Treatment with LWNT3A did not affect engraftment efficiency but analyses of programmed cell death demonstrated that L-WNT3A treated BGM$^{aged}$ had significantly fewer TUNEL$^{+ve}$ cells than L-PBS treated samples. Reduced apoptosis was also observed at post-transplant day 7. New bone formation serves as a stimulus for osteoclast-mediated bone remodeling and we observed TRAP activity around the newly formed osteoid matrix only in L-WNT3A treated BGM$^{aged}$ samples. Thus we conclude that L-WNT3A is sufficient to enhance the osteogenic capacity of BGM.

L-WNT3A Activates Stem Cells in BGMaged and Improves Bone Generation in a Spinal Fusion Model.

Figures 12A, 12B, 12C:
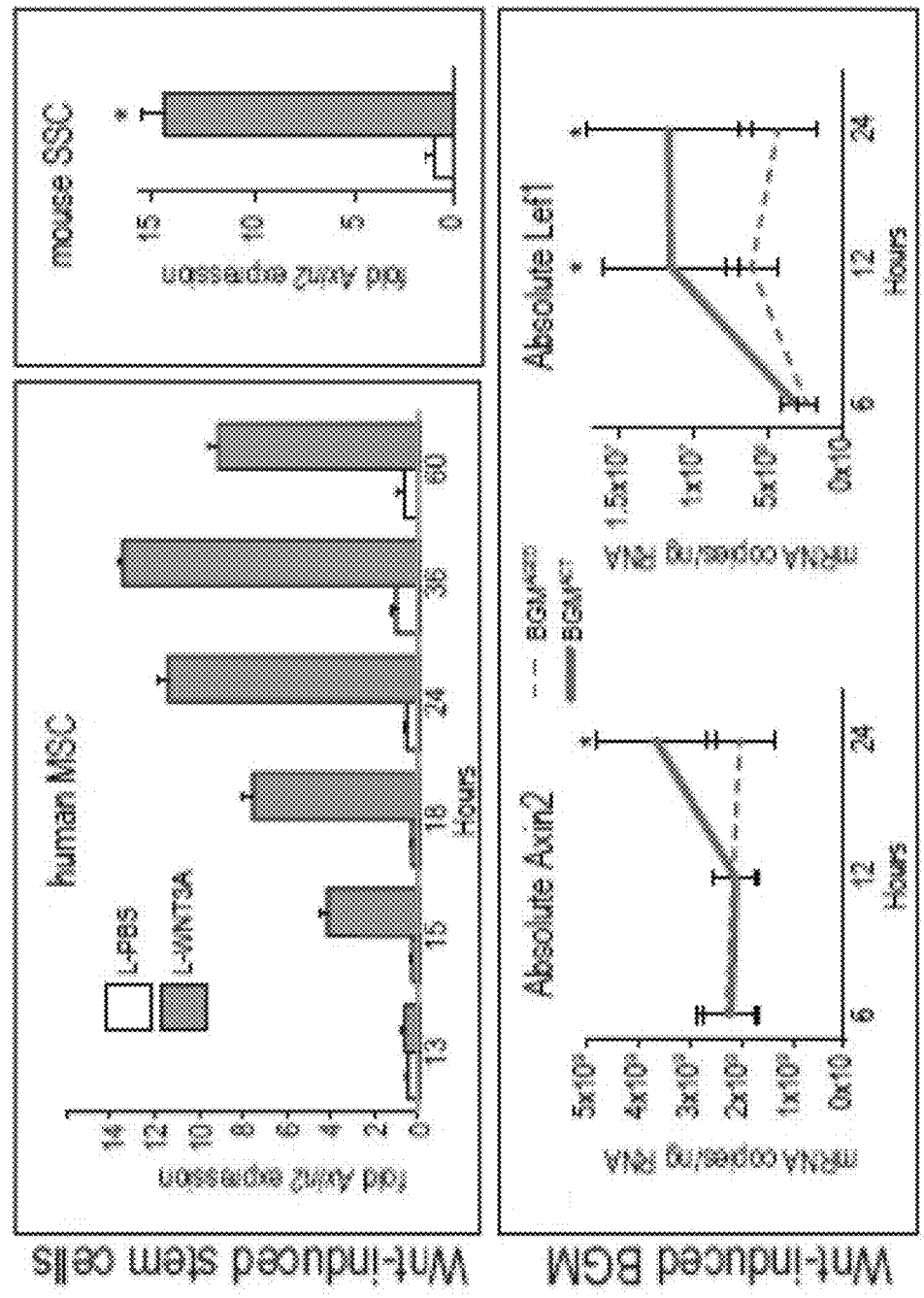
FIG. 12A-12J. L-WNT3A stimulates BGM stem cells and improves spinal fusion (FIG. 12A) Human MSC cultures were treated with L-PBS or L-WNT3A at 37° C. for the time points indicated and qRTPCR for Axin2 expression was used to determine Wnt-response.

We sought to identify the population of cells in BGM responsible for the L-WNT3A mediated surge in osteogenic capacity. We isolated three stem cell populations from BGM using standard procedures then evaluated their Wnt responsiveness using LPBS (as control) or L-WNT3A. In previous experiments we determined a dose of L-WNT3A that reliably activated Axin2 expression in stem cell populations. Time-course analyses revealed the response of stem cells to L-WNT3A treatment: within 15 h of L-WNT3A exposure a 4-fold activation in Axin2 was observed, and maximal Axin2 activation was achieved at 36 h (FIG. 12A). The effect was transient, as shown by diminished Axin2 expression in stem cells at the 60 h timepoint (FIG. 12A).

Figure 12E:
Figure 12G:
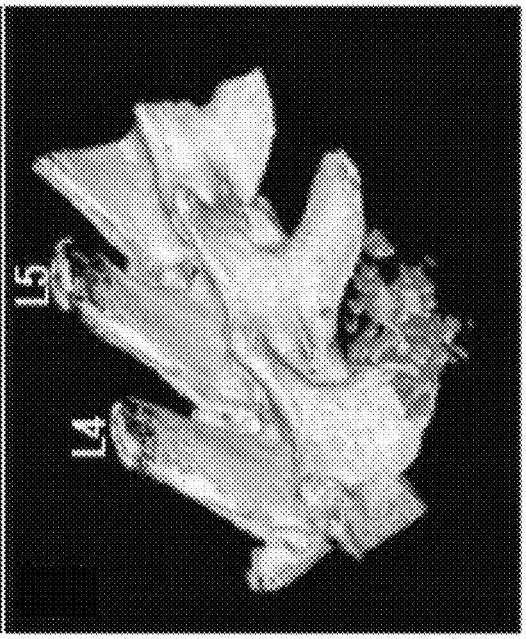
Figure 12D:
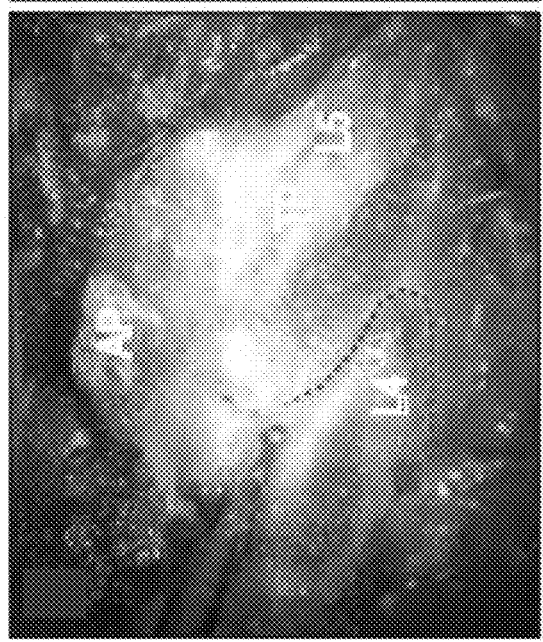
Figure 12F:
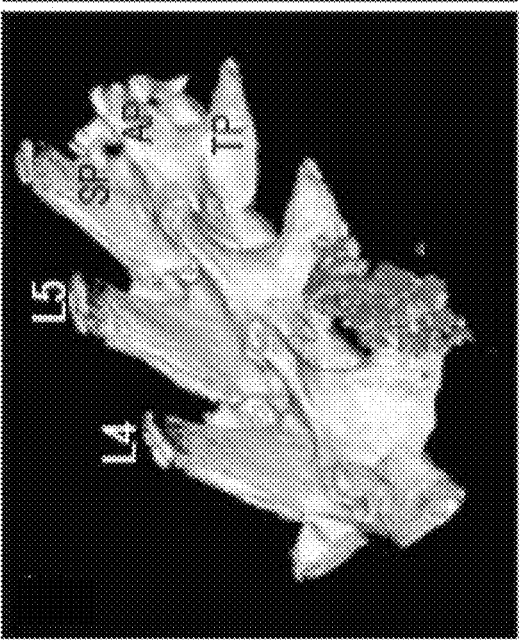
Figure 12I:
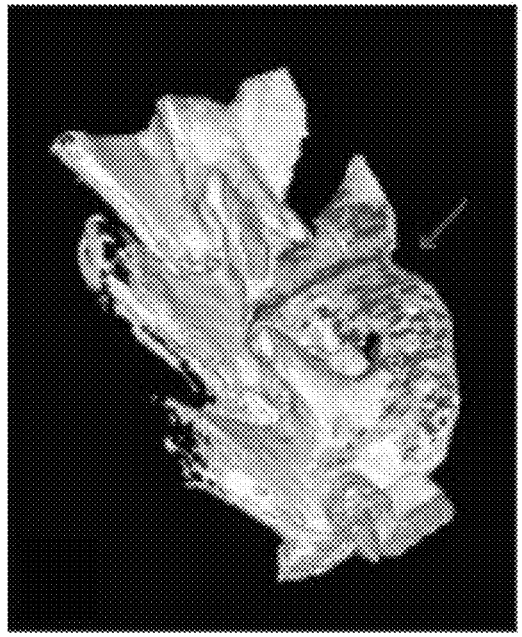
Figure 12H:
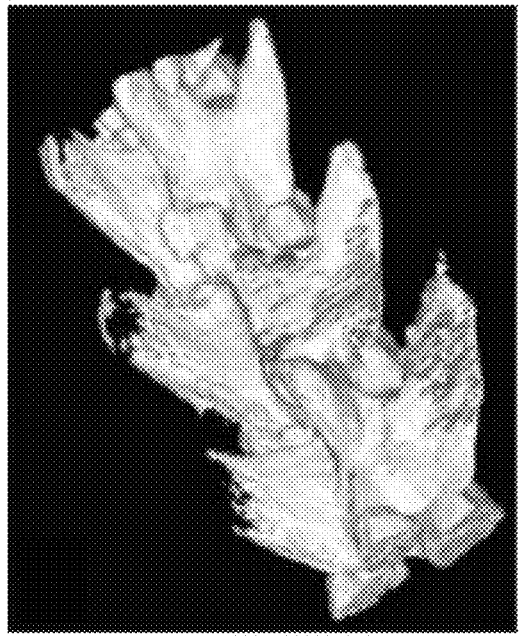
Figure 12J:
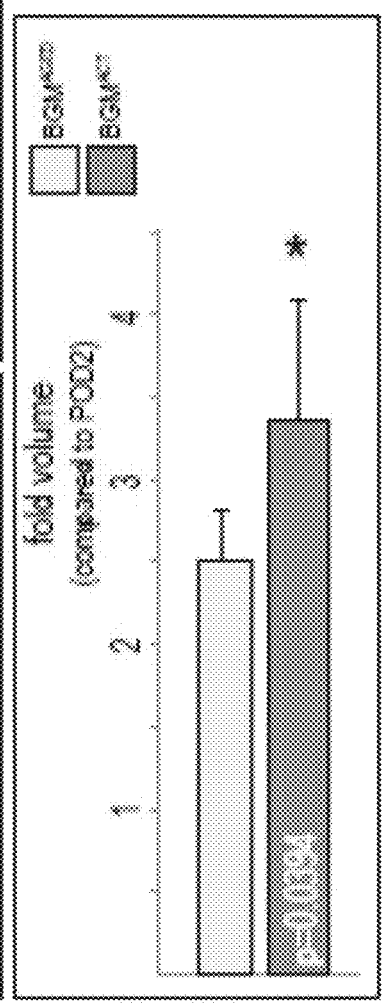

We used a second stem cell population isolated from BGM to verify that stem cells respond to L-WNT3A (FIG. 12B). The activated state of the BGM was shown by qRT-PCR. BGM$^{aged}$ was harvested, treated with L-WNT3A or L-PBS then analyzed using Axin2 and Lef1 expression for its Wnt responsive status (FIG. 12C). Within 12 h a significant elevation in Lef1 was detectable; within 24 h, both Axin2 and Lef1 were significantly elevated (FIG. 12C). These analyses confirm a WNT-mediated activation state of BGM; hereafter we refer to this material as BGM$^{ACT}$. Our next experiments tested the therapeutic potential of BGM$^{ACT}$ in a rat spinal fusion model. The transverse processes of the fourth and fifth lumbar (e.g., L4-5) vertebrae were decorticated (FIG. 12D) and during this procedure, autologous BGM$^{aged}$ from the iliac crest was harvested and treated with L-WNT3A (or L-PBS) for 1 h. The resulting material, BGM$^{ACT}$ (or BGM$^{aged}$) was then transplanted onto and between the L4-5 processes (FIG. 12E). On post-operation day 2 the volume of the BGM was evaluated by micro-CT; these analyses verified that BGM$^{aged}$ (FIG. 12F) and BGMACT (FIG. 12) contained comparable amounts of mineralized tissue at the outset. The volume of new bone formation was re-evaluated on post-operation day 49. Three dimensional reconstructions of the micro-CT data demonstrated poor bone regeneration in sites treated with BGM$^{aged}$ (grey; FIG. 12G), in agreement with similar data from elderly patients undergoing spine fusion. In contrast, sites treated with BGM$^{ACT}$ showed evidence of robust bone formation and fusion of the transverse processes (blue; FIG. 12H). The volume of new bone between the transverse processes was quantified; compared to BGM$^{aged}$, BGM$^{ACT}$ gave rise to significantly more mineralized matrix (FIG. 12I). Thus, L-WNT3A treatment improves the osteogenic capacity of autografts from aged animals.

Almost half a million bone grafting procedures are performed annually, making autografts the second most commonly transplanted tissue in the United States (AATB Annual Survey). Autografts have significant advantages over allogeneic grafts and synthetic bone substitutes, but they are contraindicated in the elderly and in patients with underlying bone or metabolic diseases. Here, we directed our efforts towards understanding the factors important for autograft efficacy, and towards validating a method that improves autograft efficacy. Four major factors influence the osteogenic capacity of an autograft: first, the site from which the autograft is harvested; second, how the autograft is handled after harvesting; third, the growth factor constituency of the autograft; and fourth, the activation state of stem cells in the autograft. Here, we provide evidence that WNT signals can influence three of these four critical variables.

Optimizing autograft harvesting and handling. The osteogenic capacity, and thus the efficacy of an autograft, is influenced by the site and method of harvest. Most non-vascularized autografts are harvested from the iliac crest but with a reamer/irrigator/aspirator (RIA) approach, the femoral and tibial medullary cavities can also be accessed. The osteogenic capacity of autografts collected via RIA and conventional harvest is equivalent. Using a simulated RIA approach we observed a distinct difference in the cellular constituency of BGM harvested from the iliac crest, the femur, and the tibia. Further, iliac crest BGM had a significantly higher level of anabolic osteogenic gene expression compared to BGM from the femur or tibia (FIG. 7). All of these BGM aliquots, however, exhibited bone-forming potential in the sub-renal capsule (SRC) assay (FIG. 7). The efficacy of an autograft can also be compromised by inappropriate handling of the material, prior to transplantation back into the patient. For example, even when freshly harvested BGM is maintained at room temperature there is significant cellular apoptosis. Treating BGM with L-WNT3A significantly improves cell survival: for example, compared to BGM alone, BGM$^{ACT}$ exhibits ~50% fewer TUNEL-positive cells. Mitotic activity is also significantly higher in BGM$^{ACT}$ v. BGM treated with L-PBS (FIG. 11D-F). Together, this increase in cell proliferation and a concomitant reduction in cell death translate into increased BGM viability and thus improved autograft efficacy.

Optimizing growth factor activity in autografts. The efficacy of an autograft also appears to depend upon the presence of growth factors in the material. In freshly harvested autografts, a wide variety of growth factors have been identified including transforming growth factor beta, bone morphogenetic proteins, vascular endothelial growth factor, and platelet-derived growth factor. In demineralized freeze-dried allografts, however, these factors are either lacking or present in minimally measurable quantities. To our knowledge there are no studies reporting the level of endogenous WNT signaling in autografts or allografts. There are, however, a number of studies clearly demonstrating that serum levels of Wnt inhibitors are elevated in the elderly, which presumably decreases Wnt signaling activity. These clinical findings are in agreement with our data showing that endogenous Wnt activity in BGM declines with age (FIG. 8). Consequently, an approach that elevates WNT responsiveness restores osteogenic capacity to autografts. We demonstrated that treatment with L-WNT3A activates Wnt signaling in the BGM, which correlates with robust osteogenesis in the SRC (FIG. 11) and in a spinal fusion model (FIG. 12).

Activating autograft stem cells with L-WNT3A. At least some of the efficacy of an autograft can be traced back to stem/stromal cells within the material. In the marrow cavity, osteogenic/skeletal stem cells are adhered to or embedded on the endosteal surface. As a consequence, harvesting methods that rely on aspiration alone typically fail to collect these adherent stem cell populations. In fact, current estimates place the number of stem cells in bone marrow aspirates as low as 1/50,000 nucleated cells; in elderly patients the number drops to only 1/1,000,000 nucleated cells. RIA harvesting intentionally removes the endosteal surface and therefore is more likely to contain the osteogenic stem cell populations. We used a modified RIA approach that removes the surface of the endosteum where Wnt responsive cells reside (FIG. 8) then demonstrated that BGM collected in this manner contains stem/progenitor cell populations and is robustly osteogenic (FIG. 7), specifically because of the endogenous Wnt signal (FIG. 10).

Autografts continue to represent the classic exemplar for bony reconstruction; there still remains, however, considerable room for improvement in autograft efficacy. Data shown here demonstrate that ex vivo exposure to L-WNT3A improves cell viability and activates stem cell populations in freshly harvested autografts, which culminates in increased osteogenic activity. These data have direct clinical application, especially for autografts from at-risk patient populations whose inherent bone forming capacity is reduced by illness, disease, or aging.

---

What is claimed is:

1. A method of repairing a bone, comprising:
   (a) obtaining a bone graft material from a subject in need thereof;
   (b) contacting the bone graft material ex-vivo with a liposome comprising a Wnt protein to produce a modified human bone graft material; and
   (c) administering the modified bone graft material to the bone of the subject, wherein the subject receives a spinal fusion.

2. The method of claim 1, wherein the Wnt protein is a Wnt3a protein.

3. The method of claim 1, wherein the bone graft material comprises bone marrow stem cells or bone marrow progenitor cells.

4. The method of claim 1, wherein the bone graft material comprises mesenchymal stem cells or osteocytes.

5. The method of claim 1, wherein the bone graft material is taken from a site other than a site of the spinal fusion.

6. The method of claim 1, wherein contacting comprises incubating the bone graft material with the liposome comprising the Wnt protein.

7. The method of claim 6, wherein the incubating is for a time up to one hour.

8. The method of claim 6, wherein the incubating is for a time up to 36 hours.

9. The method of claim 1, wherein contacting is at room temperature.

10. The method of claim 1, wherein contacting is at about 37° C.

11. The method of claim 1, wherein the bone is associated with a bone disease.

12. The method of claim 1, wherein the bone is associated with a metabolic disease.

13. The method of claim 1, wherein the bone is associated with fatty degeneration.

14. The method of claim 1, wherein the bone graft material from the subject comprises tissue associated with fatty degeneration.

15. The method of claim 1, wherein the subject is a human.

16. The method of claim 1, wherein the bone graft material is obtained from iliac crest.

17. The method of claim 1, wherein the modified bone graft material is administered to the subject subsequent to a spinal fusion procedure.

18. The method of claim 1, wherein the modified bone graft material is administered to the subject concurrently with a spinal fusion procedure.

* * * * *

SEQUENCE LISTING

<160> NUMBER OF SEQ ID NOS: 14

<210> SEQ ID NO 1
<211> LENGTH: 352
<212> TYPE: PRT
<213> ORGANISM: Homo sapiens

<400> SEQUENCE: 1

```
Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
    50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
    290                 295                 300

Asp Gly Cys Asp Leu Leu Cys Cys Gly Arg Gly His Asn Ala Arg Ala
```

```
                305                 310                 315                 320
Glu Arg Arg Arg Glu Lys Cys Arg Cys Val Phe His Trp Cys Tyr
                    325                 330                 335
Val Ser Cys Gln Glu Cys Thr Arg Val Tyr Asp Val His Thr Cys Lys
                340                 345                 350

<210> SEQ ID NO 2
<211> LENGTH: 1555
<212> TYPE: DNA
<213> ORGANISM: Homo sapiens

<400> SEQUENCE: 2
cggcgatggc cccactcgga tacttcttac tcctctgcag cctgaagcag gctctgggca      60
gctacccgat ctggtggtcg ctggctgttg ggccacagta ttcctccctg ggctcgcagc     120
ccatcctgtg tgccagcatc ccgggcctgg tccccaagca gctccgcttc tgcaggaact     180
acgtggagat catgcccagc gtggccgagg catcaagat ggcatccag gagtgccagc      240 accagttccg cggccgccgg tggaactgca ccaccgtcca cgacagcctg gccatcttcg     300
ggcccgtgct ggacaaagct accagggagt cggcctttgt ccacgccatt gcctcagccg     360
gtgtggcctt tgcagtgaca cgctcatgtg cagaaggcac ggccgccatc tgtggctgca     420
gcagccgcca ccagggctca ccaggcaagg gctggaagtg gggtggctgt agcgaggaca     480
tcgagtttgg tgggatggtg tctcgggagt tcgccgacgc ccgggagaac cggccagatg     540
cccgctcagc catgaaccgc acaacaacg aggctgggcg ccaggccatc gccagccaca      600
tgcacctcaa gtgcaagtgc acgggctgt cgggcagctg cgaggtgaag acatgctggt      660
ggtcgcaacc cgacttccgc gccatcggtg acttcctcaa ggacaagtac gacagcgcct     720
cggagatggt ggtggagaag caccgggagt cccgcgctg ggtggagacc ctgcggccgc      780
gctacaccta cttcaaggtg cccacggagc gcgacctggt ctactacgag gcctcgccca     840
acttctgcga gcccaacccct gagacgggct ccttcggcac gcgcgaccgc acctgcaacg     900
tcagctcgca cggcatcgac ggctgcgacc tgctgtgctg cggccgcggc acaacgcgc      960 gagcggagcg gcgccgggag aagtgccgct gcgtgttcca ctggtgctgc tacgtcagct    1020
gccaggagtg cacgcgcgtc tacgacgtgc acacctgcaa gtaggcaccg ccgcggctc     1080 cccctggacg gggcgggccc tgcctgaggg tgggcttttc cctgggtgga gcaggactcc    1140
cacctaaacg gggcagtact cctccctggg ggcgggactc ctccctgggg gtggggctcc    1200
tacctggggg cagaactcct acctgaaggc agggctcctc cctggagcta gtgtctcctc    1260
tctggtggct gggctgctcc tgaatgaggc ggagctccag gatggggagg ggctctgcgt    1320
tggcttctcc ctggggacgg ggctcccctg gacagaggcg gggctacaga ttgggcgggg    1380
cttctcttgg gtgggacagg gcttctcctg cggggggcgag gcccctccca gtaagggcgt    1440
ggctctgggt gggcggggca ctaggtaggc ttctacctgc aggcggggct cctcctgaag    1500
gaggcggggc tctaggatgg ggcacggctc tggggtaggc tgctccctga gggcg          1555

<210> SEQ ID NO 3
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 3
tcattttccg agaacccacc gc                                                22
```

<210> SEQ ID NO 4
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 4
gctccagttt cagtttctcc agcc                                           24

<210> SEQ ID NO 5
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 5
aggagcccaa aagacctcat                                                20

<210> SEQ ID NO 6
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 6
cgtgcactca gctatgacat                                                20

<210> SEQ ID NO 7
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 7
acccagaaga ctgtggatgg                                                20

<210> SEQ ID NO 8
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 8
ggatgcaggg atgatgttct                                                20

<210> SEQ ID NO 9
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 9
accttgactg tggttactgc                                                20

<210> SEQ ID NO 10
<211> LENGTH: 21
<212> TYPE: DNA
<213> ORGANISM: Artificial sequence
<220> FEATURE:

```
<223> OTHER INFORMATION: synthetic polynucleotide

<400> SEQUENCE: 10
catataggat ggccgtgaag g                                              21

<210> SEQ ID NO 11
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 11
ggagaccttg ctcgtagatt tc                                             22

<210> SEQ ID NO 12
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 12
gggatcttag tgactgccta ac                                             22

<210> SEQ ID NO 13
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 13
tgtgacgagc tatcaaacca g                                              21

<210> SEQ ID NO 14
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 14
gaggatcaag ttctggagag c                                              21
```